(12) United States Patent
Kim et al.

(10) Patent No.: US 6,360,651 B1
(45) Date of Patent: Mar. 26, 2002

(54) HOME-STYLE DECOCTOR ENDOWED WITH STEAMY BOILING FUNCTION, AND METHOD OF PREPARING RED GINSENG EXTRACT USING THE SAME

(75) Inventors: Yong Jin Kim; Joon Hwan Kim; Byung Gil Lee, all of Seoul (KR)

(73) Assignee: Daewoong Electric Industrial Co., Ltd. (KR)

( * ) Notice: Subject to any disclaimer, the term of this patent is extended or adjusted under 35 U.S.C. 154(b) by 0 days.

(21) Appl. No.: 09/651,992

(22) Filed: Aug. 30, 2000

(30) Foreign Application Priority Data

| Aug. 31, 1999 | (KR) | 99-36486 |
| Dec. 23, 1999 | (KR) | 99-60810 |
| Dec. 24, 1999 | (KR) | 99-61843 |

(51) Int. Cl.[7] ............... A47J 37/04; A47J 27/04; A61L 2/00
(52) U.S. Cl. ............... 99/293; 99/285; 99/317; 99/342; 99/403; 99/417; 219/433; 422/295; 422/298; 422/300
(58) Field of Search .......... 99/330, 341, 342, 99/285, 288, 304, 305, 306, 293, 316, 317, 403, 407, 410, 415, 418, 417, 450, 467, 468, 483; 126/369, 20, 377, 378, 384, 389, 246, 262

(56) References Cited

U.S. PATENT DOCUMENTS

| 4,759,275 A | * | 7/1988 | Lee ............... 99/317 |
| 5,931,082 A | * | 8/1999 | Kim et al. ....... 99/342 |
| 6,112,643 A | * | 9/2000 | Lee ............... 99/293 |

* cited by examiner

Primary Examiner—Reginald L. Alexander
(74) Attorney, Agent, or Firm—F. Chau & Associates LLP

(57) ABSTRACT

A home-style decoctor endowed with steamy boiling function includes a main body equipped with a heater; a heating vessel; a support plate for allowing a to-be-boiled object to be placed above the surface of the water stored in the heating vessel; a water supply for supplying water for boiling into the heating vessel so that the to-be-object is immersed; a steam collector for gathering stream produced when the to-be-boiled object is decocted with water; a condenser for condensing the steam collected into the steam collector; and a stream/condensed water guide for leading the steam present in the heating vessel to the steam collector and the condensed water placed in the steam collector to the heating vessel. With such construction, undried or white ginseng can become red ginseng extract by producing such useful components as several kinds of phenolic compounds and maltol, anti-oxidants, and ginsenosides Rg and Rh through steam-boiling, drying and re-boiling.

31 Claims, 20 Drawing Sheets

PRIOR ART

PRIOR ART

HOME-STYLE DECOCTOR ENDOWED WITH STEAMY BOILING FUNCTION, AND METHOD OF PREPARING RED GINSENG EXTRACT USING THE SAME

FIELD OF THE INVENTION

The present invention relates to a home-style decoctor and a method of preparing red ginseng extract using the same. More particularly, this invention pertains to a home-style decoctor endowed with steamy boiling function, the decoctor heating and boiling (undried, white or red) ginseng to draw out red ginseng extract, the invention further applying to a method of preparing red ginseng extract.

BACKGROUND OF THE INVENTION

Generally speaking, Panax ginseng is a medicinal herb used as hematinic tonic medicine for a long time in the eastern Asia. Korean ginseng is especially known to contain a great quantity of more than thirty kinds of ginsenoside.

Grubbed up after the cultivation of four to six years, panax ginseng is classified into undried (unprocessed and containing water as much as 70 to 80%), white (the primarily processed product), and finally red ginseng according to the processing method.

White ginseng is made by being dried with or without the skin of undried ginseng of over four years, the white containing water below 12%. Red ginseng is manufactured by steam-boiling undried ginseng for the purpose of long-time preservation or according to another process.

The red ginseng has several kinds of phenolic compounds and maltol, aging-resistants (anti-oxidants), and ginsenosides Rg and Rh, all of which are produced through a steamy boiling process but not contained in undried ginseng, as well as a great volume of more than thirty kinds of ginsenoside. The red ginseng is known to further have a great quantity of ginsenosides, its peculiar components, and panaxydol group and panaxytriol group.

Red ginseng made as above may be produced as ginseng extract, which is drawn out with several components of red ginseng. The extract can be drunk as a undiluted solution or an alkaline which is made by adding raw medicinal stuff or physiological activator thereto.

It is difficult to domestically make red ginseng extract because of several complicated processes as described above. Even though it is made domestically, charcoal is used to decoct the red ginseng, which is also not simple. Because of those problems, there has been developed a decoctor for facilitating the domestic decoction of ginseng or other objects.

FIG. 1 is a vertical section of a conventional home-style decoctor; FIG. 2 is an enlarged vertical section of the heating vessel of the conventional decoctor; and FIG. 3 is an enlarged vertical section of the steam condensing means of the decoctor.

Referring to FIGS. 1, 2 and 3, a prior art decoctor 10 has: a main body 20 equipped with a heater 22 at an appropriate place; a heating vessel 30 which stores water and is heated by heater 22; a filter 32 positioned in heating vessel 30 and for containing an object to be boiled (for instance, undried, white or red ginseng); a steam collector 40 for gathering steam generated from heating vessel 30 during the decoction of the object; means for cooling steam collector 40 with cooling water; and steam/condensed water guiding means for enabling heating vessel 30 to communicate with steam collector 40 when heating vessel 30 is safely placed in main body 20, and thus leading the steam contained in heating vessel 30 to steam collector 40 and the condensed water condensed in steam collector 40 to heating vessel 30.

With the conventional home-style decoctor 10, when heater 22 is operated while heating vessel 30 containing an object to be boiled and a predetermined amount of water is mounted thereon, the to-be-boiled object contained in heating vessel 30 is decocted due to heater 22 heated. This to-be-boiled object is heated while immersed in water stored in heating vessel 30. The steam produced in heating vessel 30 during the decoction goes into steam collector 40 by means of the steam guiding means, and the steam collected in steam collector 40 and then condensed by the cooling means in turn to heating vessel through steam/condensed water guiding means 50.

The decoction of a to-be-boiled object and its extraction is carried out through the repeated performance of incoming of the steam produced from heating vessel 30, which is heated, into steam collector 40 and heating vessel 30 in the form of steam or condensed water.

In case of red ginseng extraction through the decoction of undried or white ginseng with the conventional home-style decoctor, however, the undried or white ginseng is designed to be decocted while immersed into water stored in the heating vessel. In this condition several kinds of phenolic compounds and maltol as aging-resistants (anti-oxidants) and ginsenosides Rg and Rh are not produced, which are, however, contained only in red ginseng. This is because there is no steamy boiling in the conventional decoctor.

SUMMARY OF THE INVENTION

Therefore, in order to overcome such drawbacks of the prior art, an objective of the present invention is to provide a home-style decoctor endowed with a steamy boiling function, with which ginseng (undried or white) is steam-boiled to become red ginseng and thus generate several kinds of phenolic compounds and maltol, aging-resistants (anti-oxidants), and ginsenosides Rg and Rh. This invention also aims for a method of preparing a red ginseng extract using the decoctor of the invention.

To accomplish the objectives of the present invention, there is provided a home-style decoctor endowed with steamy boiling function, the decoctor being comprised of: a main body of a predetermined size equipped with a heater at an appropriate position of the bottom; a heating vessel for containing and heating a predetermined amount of water with the heater; a support plate having a plurality of through-holes and for allowing a to-be-boiled object to be placed above the surface of water stored in the heating vessel and to be steam-boiled with the steam produced inside the heating vessel; means for supplying water for boiling into the heating vessel so that the to-be-object is immersed after its steamy boiling and drying; a steam collector for gathering steam produced when the to-be-boiled object is decocted with water for boiling poured in the heating vessel which stores the water for boiling through the water for boiling supplying means; means for condensing the steam collected into the steam collector; and steam/condensed water guiding means for causing the heating vessel to communicate with the steam collector when the heating vessel is safely placed in the main body and thus leading the steam present in the heating vessel to the steam collector and the condensed water placed in the steam collector to the heating vessel.

There is provided another embodiment of a home-style decoctor endowed with steamy boiling function of the present invention comprising: a main body of a predetermined size having a heater at an appropriate place of its bottom; a heating vessel put above the heater for heating a to-be-boiled object contained therein; a support plate having a plurality of throughholes mounted on the heater for supporting a to-be-boiled object so that it is located above water stored, the plate allowing the object to be steam-boiled by means of steam produced inside the heating vessel; a water reservoir installed at an appropriate place of the main body for storing water to be supplied to the heating vessel; means for supplying water stored in the water reservoir to the heating vessel; a steam collector for gathering steam produced from the heating vessel while the object contained in the heating vessel is boiled; means for condensing the steam collected in the steam collector; and steam/condensed water guiding means for enabling the heating vessel to communicate with the steam collector when the heating vessel is safely placed in the main body, and thus leading the steam contained in the heating vessel to the steam collector and the water condensed in the steam collector to the heating vessel.

For another aspect of the present invention, there is provided a method of preparing red ginseng extract using a home-style decoctor comprising a main body, a heating vessel which stores water, a support plate for enabling a to-be-boiled object to be located above water stored, a water-for-boiling tank, a steam collector for gathering steam, means for condensing the steam collected in the steam collector, and steam/condensed water guiding means for leading the steam contained in the heating vessel to the steam collector and the water condensed in the steam collector to the heating vessel, the method comprising the steps of: safely placing the support plate having ginseng in the heating vessel, and storing water in the heating vessel so high that the ginseng is not immersed; storing water in the water-for-boiling tank so high as to cause the ginseng contained in the heating vessel to be immersed; steam-boiling for a predetermined time the ginseng by means of steam produced in the heating vessel heated; supplying water to the heating vessel so high as to cause the steam-boiled ginseng to be immersed; and heating the heating vessel while the steam-boiled ginseng is immersed, for the purpose of re-boiling it for a predetermined time.

There is provided another method of preparing red ginseng extract using home-style decoctor endowed with steamy coiling function having a main body, a heating vessel for heating a to-be-boiled object, a water reservoir for storing water to be supplied to the heating vessel, a support plate for allowing a to-be-boiled object to be placed above the surface of water stored in the heating vessel, means for supplying water stored in the water reservoir to the heating vessel, a steam collector for gathering steam produced from the heating vessel while the object is boiled, means for condensing the steam collected into the steam collector, and steam/condensed water guiding means for allowing the heating vessel and steam collector to communicate therebetween when the heating vessel is safely placed in the main body, the guiding means leading the steam present in the heating vessel to the steam collector and the condensed water placed in the steam collector to the heating, the method comprising the steps of: safely placing the support plate in the heating vessel; storing water in the heating vessel through the water supply means so high as not to cause ginseng to be immersed; heating the heating vessel for the purpose of steamy boiling of ginseng carried out by means of the steam produced; supplying water to the heating vessel by means of the water supply means so high that the steam-boiled ginseng is immersed; and heating the heating vessel while the steam-boiled ginseng contained in the heating vessel is immersed in water, for the purpose of re-boiling the ginseng for a predetermined time.

BRIEF DESCRIPTION OF THE ATTACHED DRAWINGS

These and other features of the invention will be understood more clearly from the following description, read in conjunction with the drawings, in which.

Figure 12A:
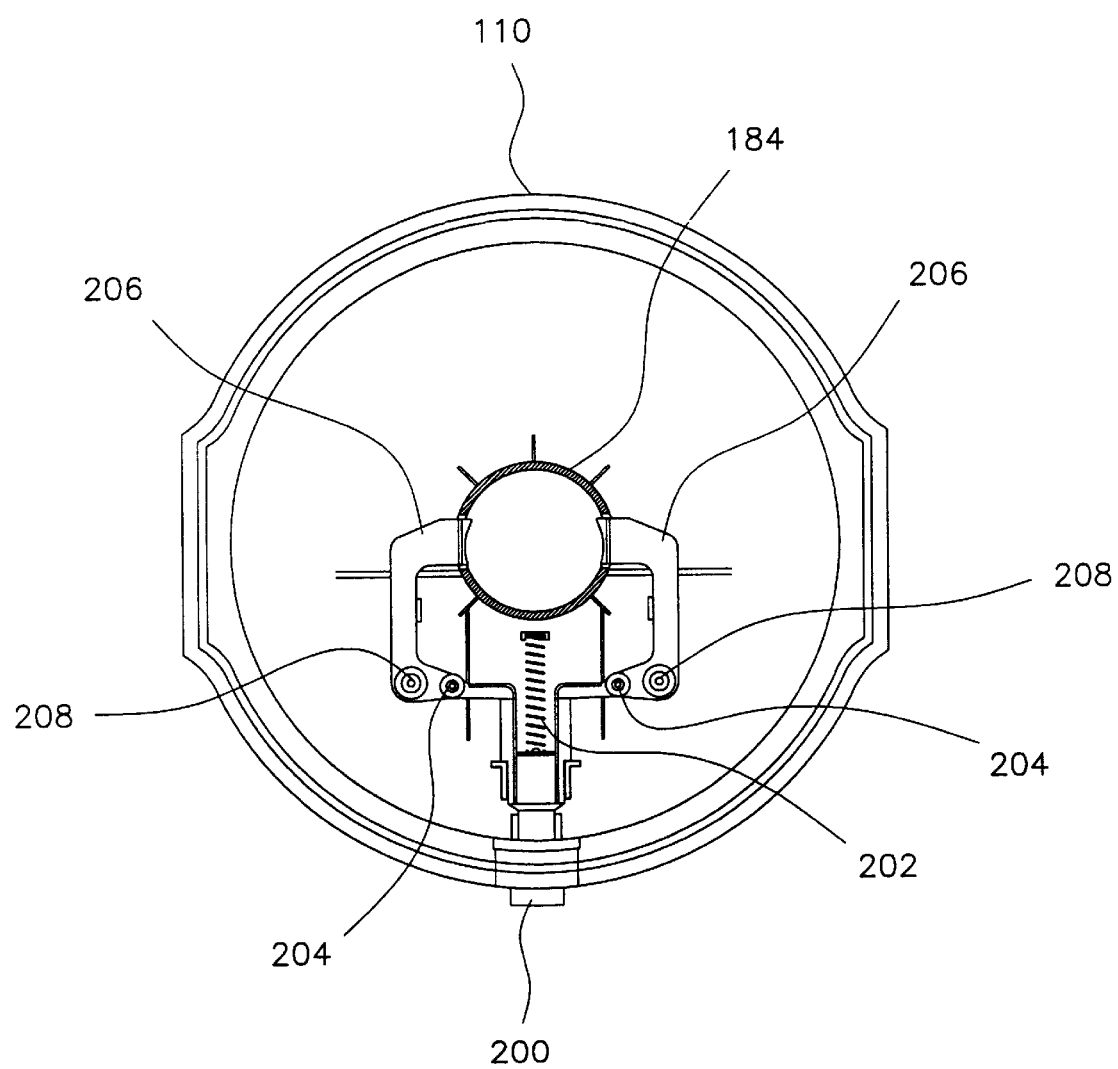
Figure 12B:
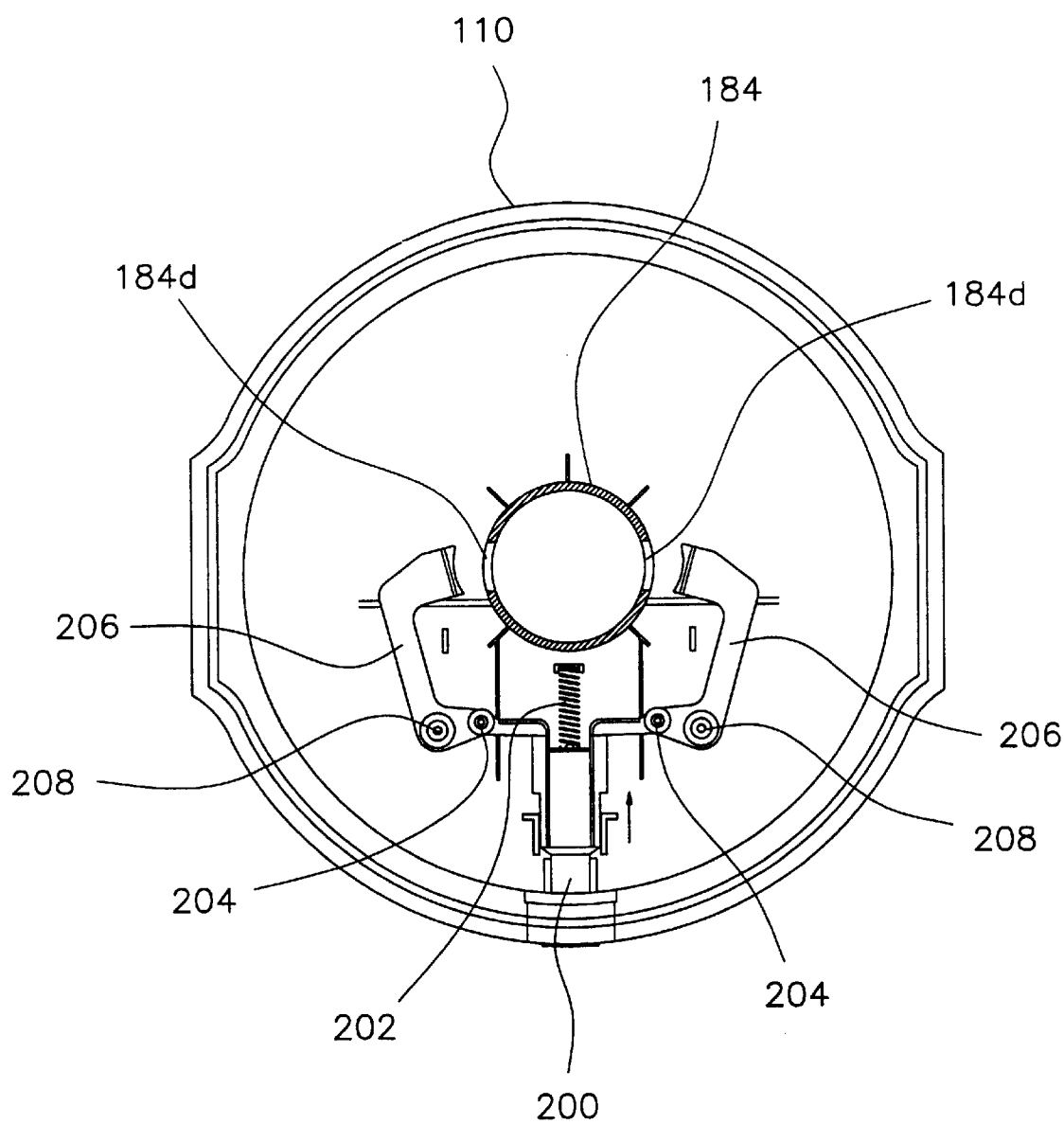
Figure 13A:
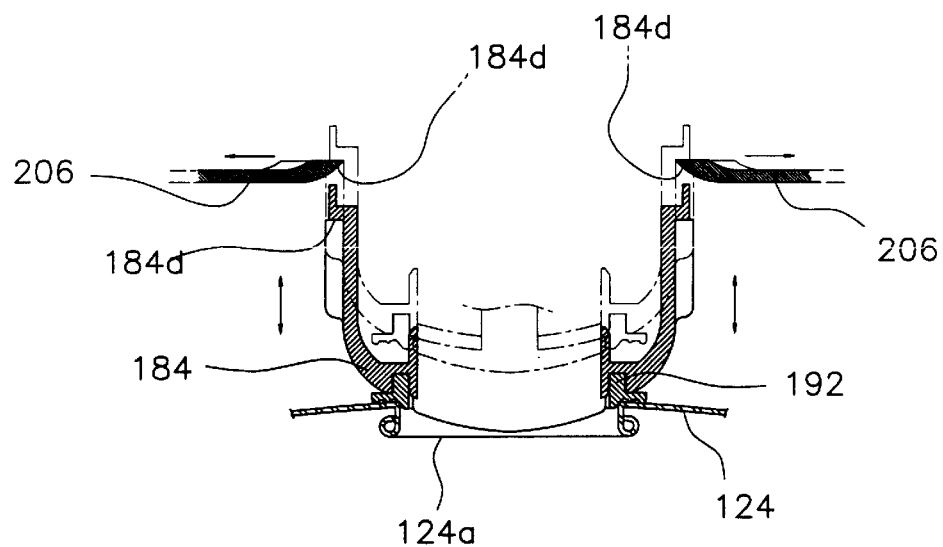
Figure 13B:
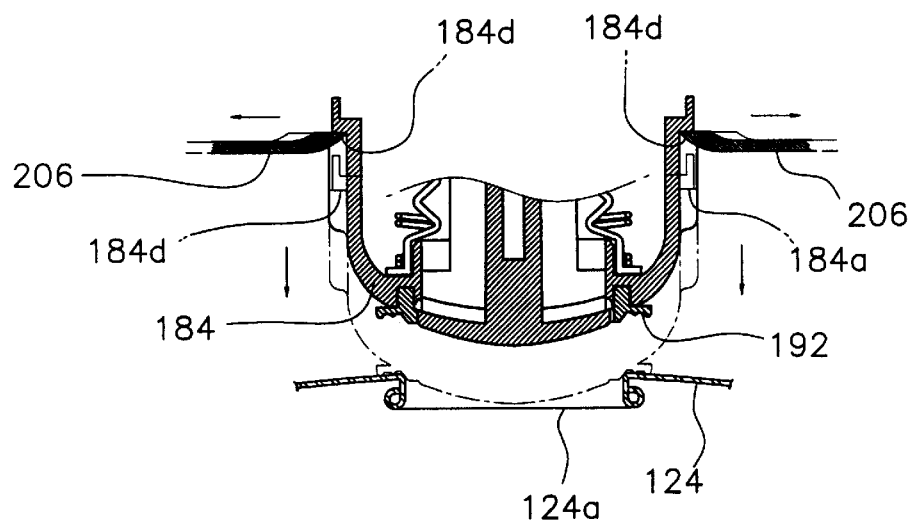
Figure 14:
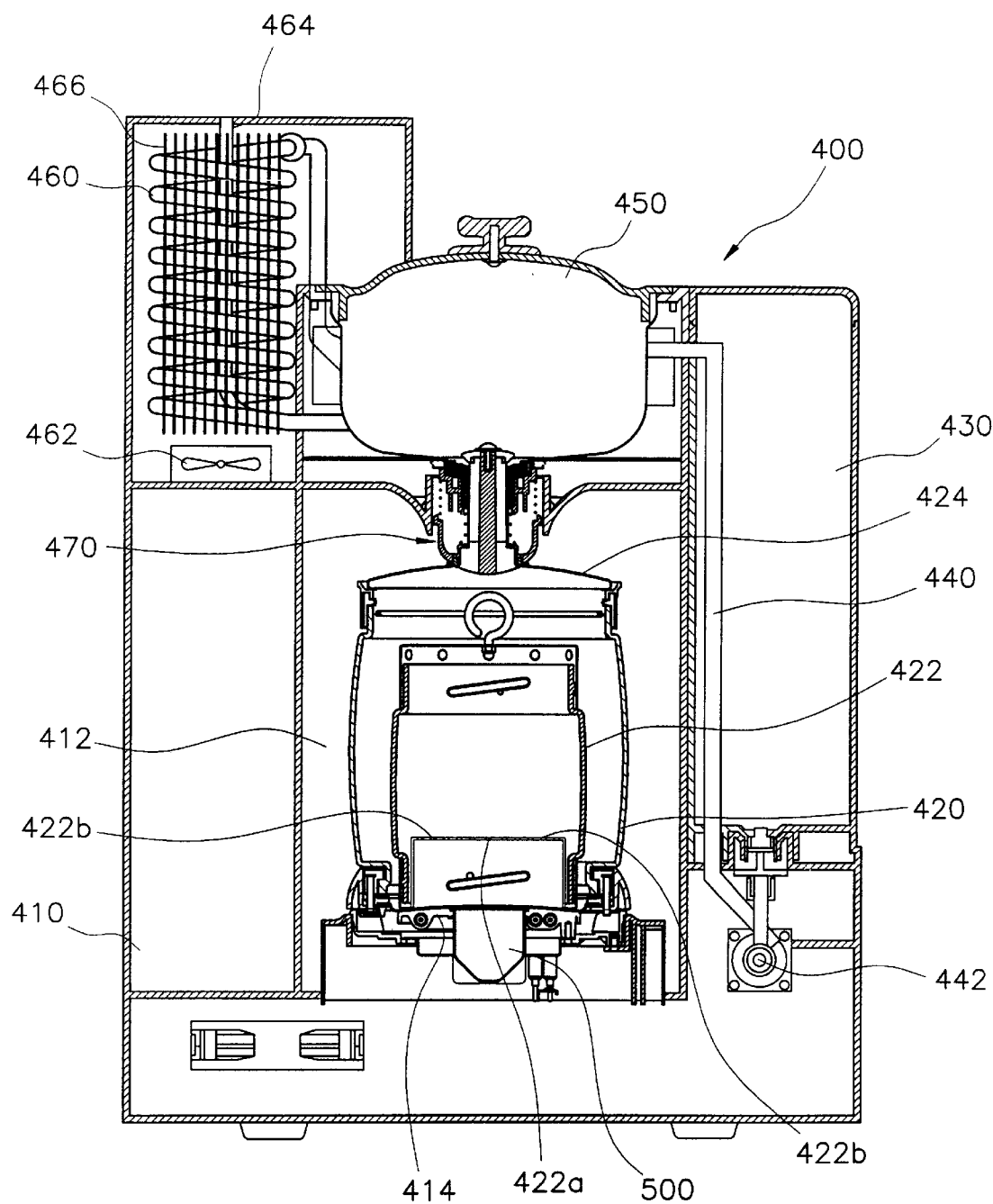
Figure 15:
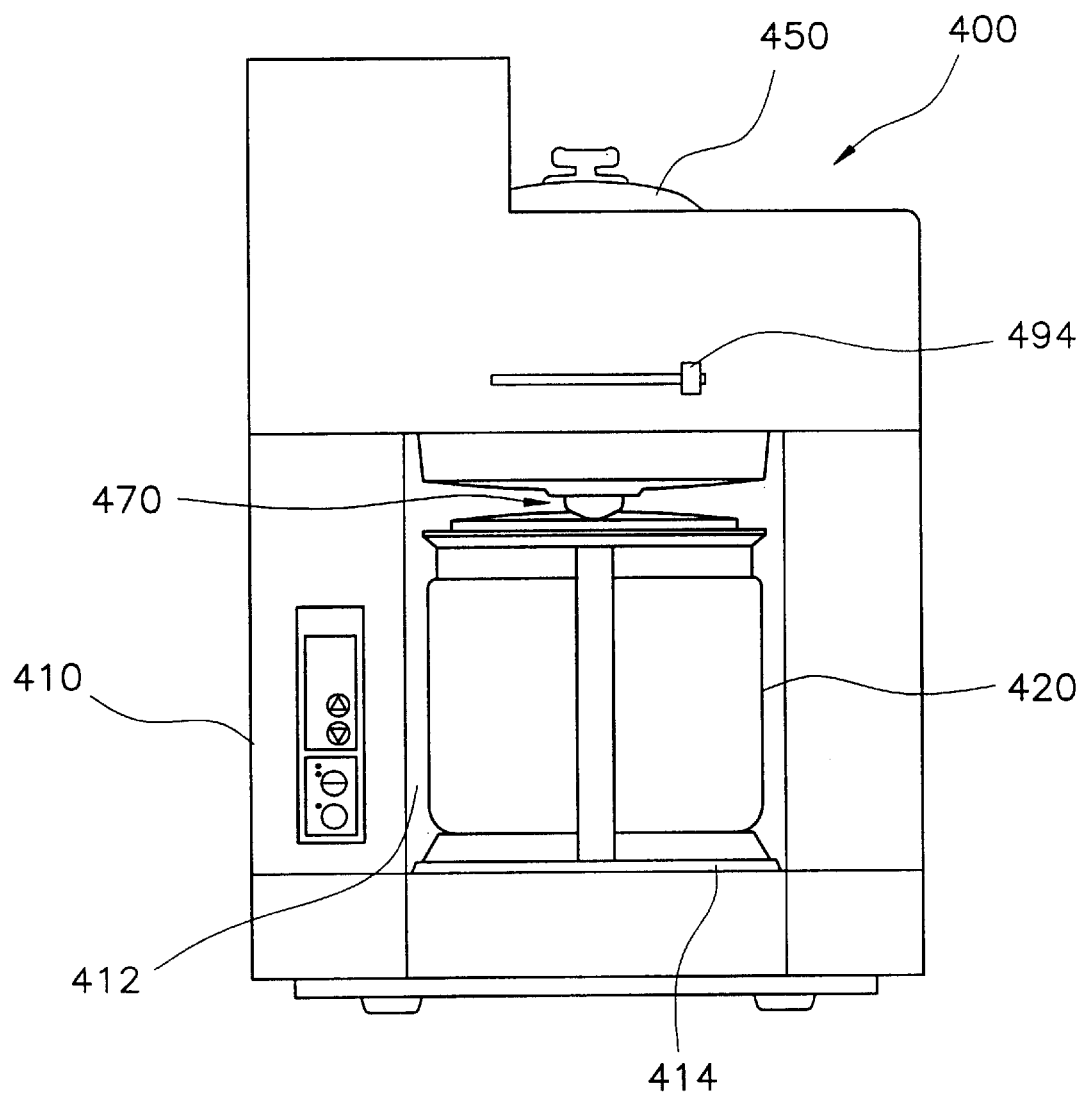
Figure 16:
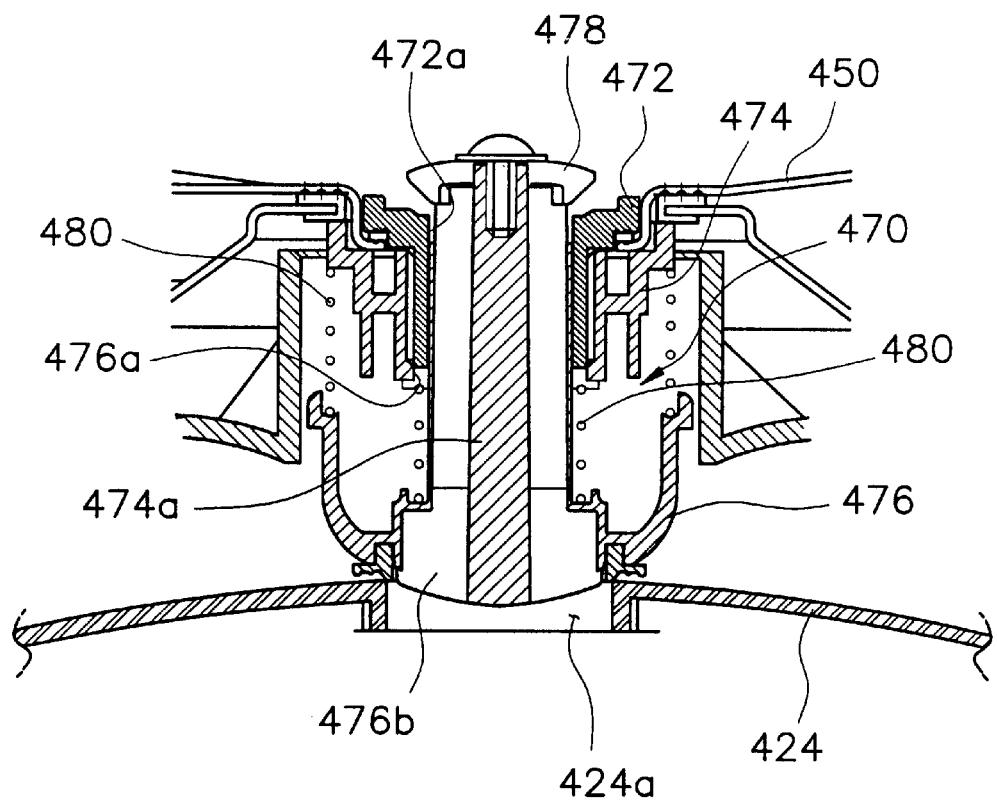
Figure 17:
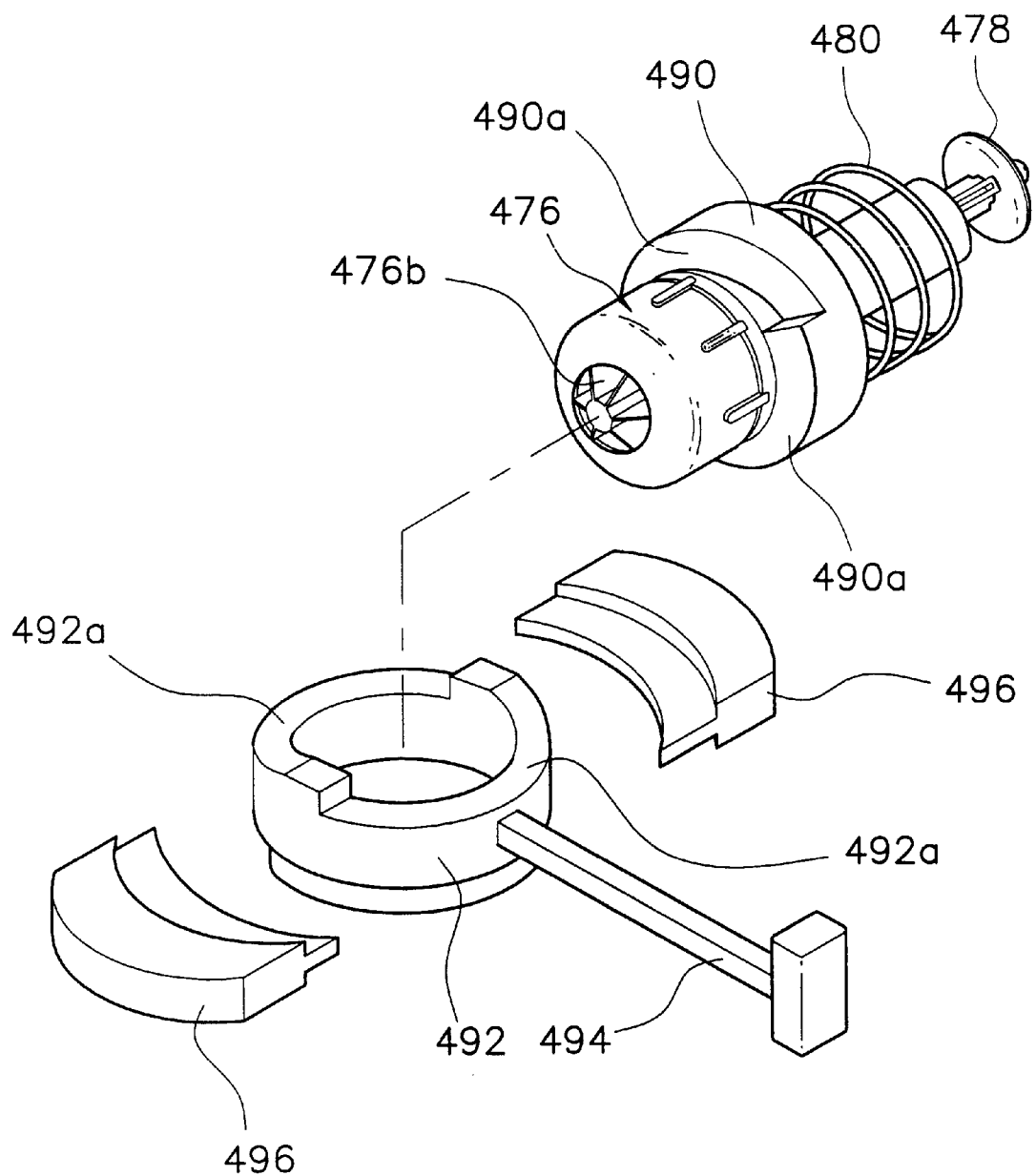
Figure 18A:
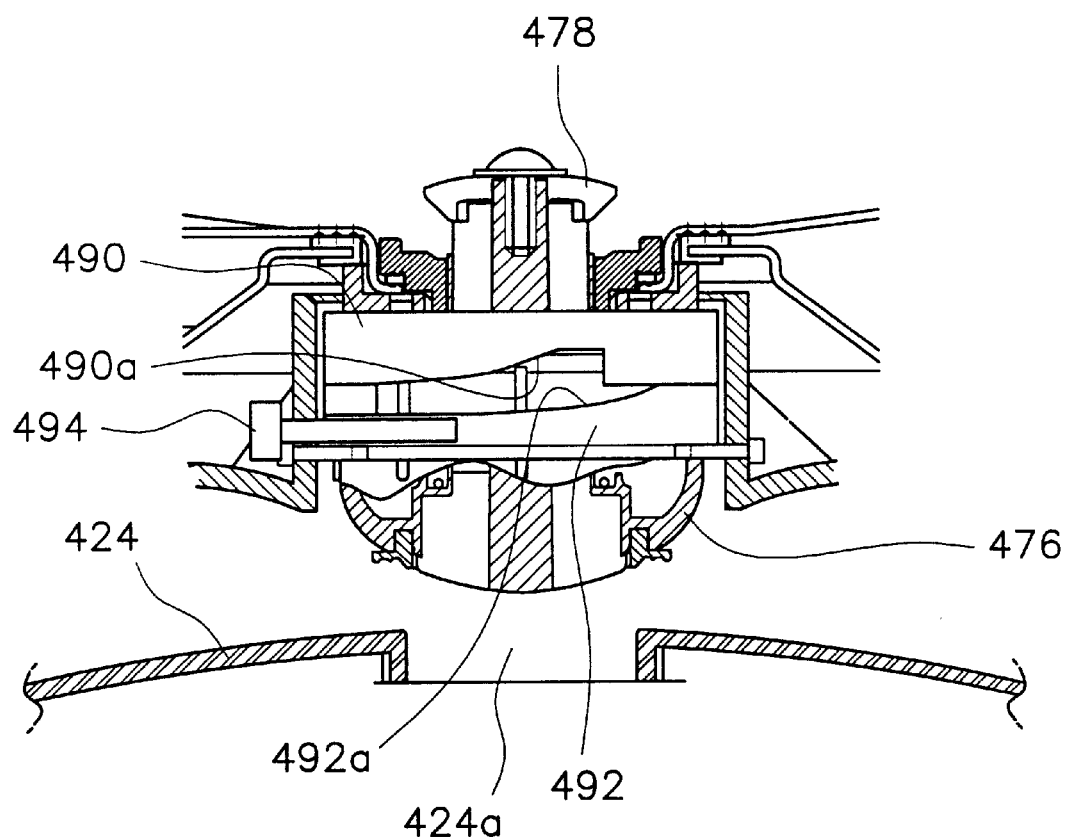
Figure 18B:
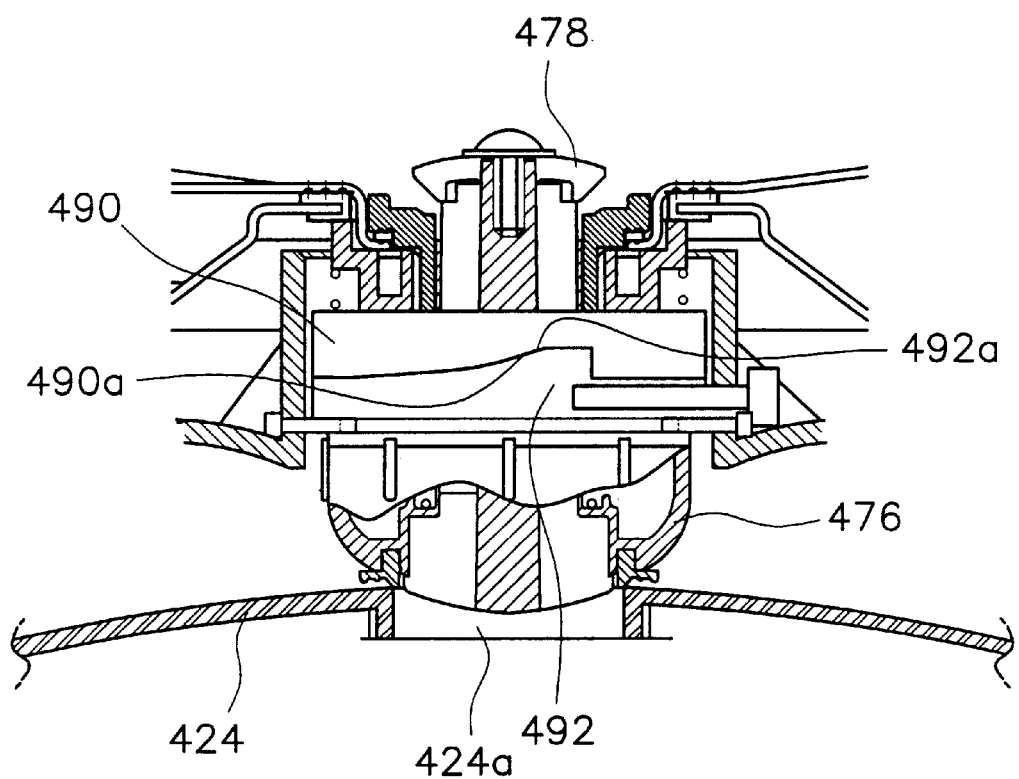

FIGS. 12a and 12b each are plans of the steam guiding portion arrester of the invention, showing its operation;

FIGS. 13a and 13b each are schematic vertical sections of the arrester of the invention, showing its operation;

FIG. 14 is a vertical section of another embodiment of the decoctor endowed with a steamy boiling function of the present invention, the embodiment being operated in an air-cooling manner;

FIG. 15 is an elevation of the air-cooled decoctor shown in FIG. 14;

FIG. 16 is a vertical section of the steam/condensed water guiding means in the air-cooled decoctor;

FIG. 17 is a vertical section of the lift of the steam/condensed water guiding means in the air-cooled decoctor; and FIGS. 18a and 18b are vertical sections showing the steam/condensed water guiding means operated according to the lift in the air-cooled decoctor, respectively.

DETAILED DESCRIPTION OF THE INVENTION

Though generally implying undried, white or red, the term 'ginseng' indicates undried or white in this invention. As far as the word 'red' is not used, the term 'ginseng' designates undried or white through the description.

Hereinafter, preferred embodiments of the home-style decoctor endowed with steamy boiling function and the method of preparing red ginseng extract of the invention are described in detail with respect of the attached drawings.

Figure 1:
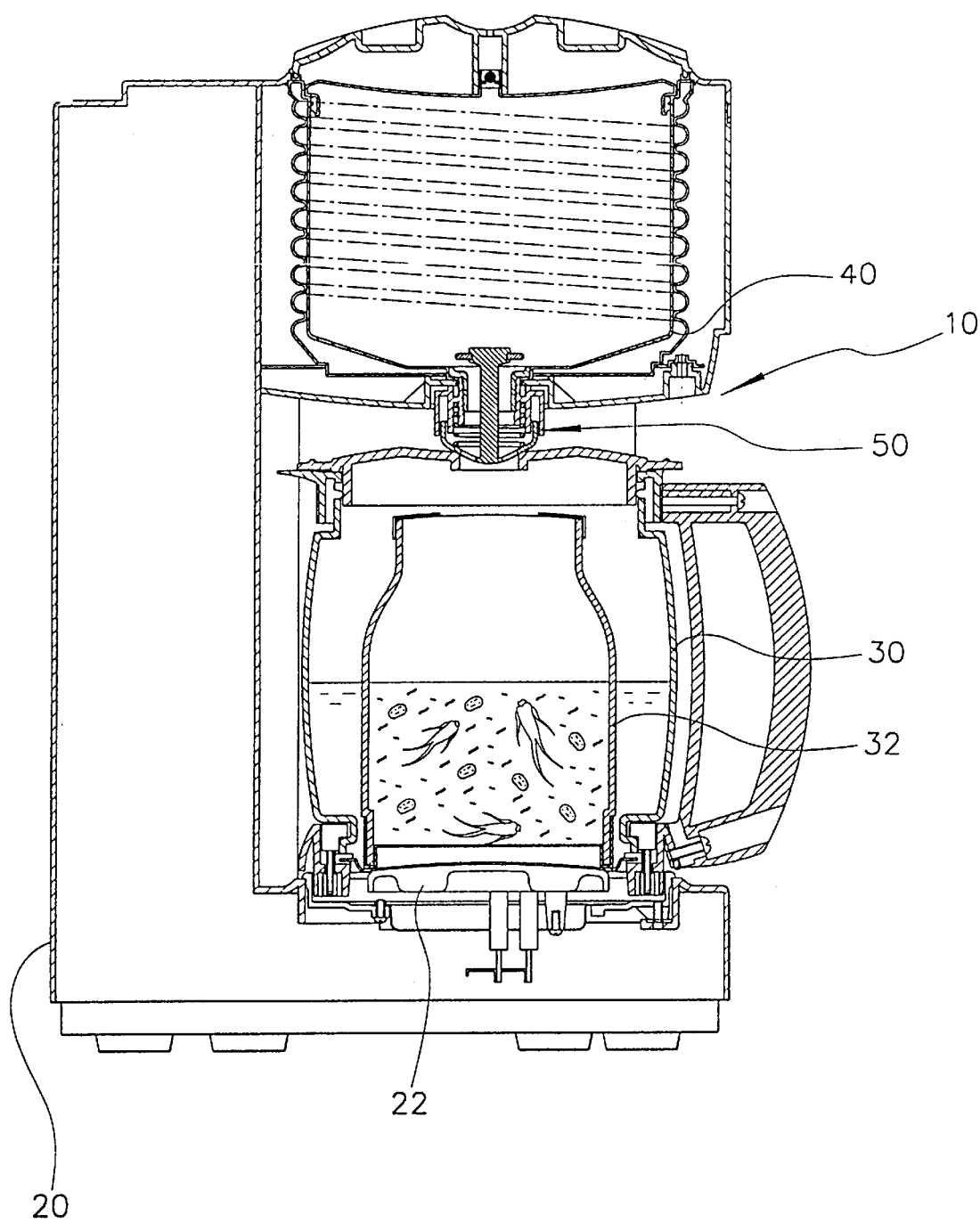
FIG. 1 is a vertical section of a conventional home-style decoctor.
Figure 2:
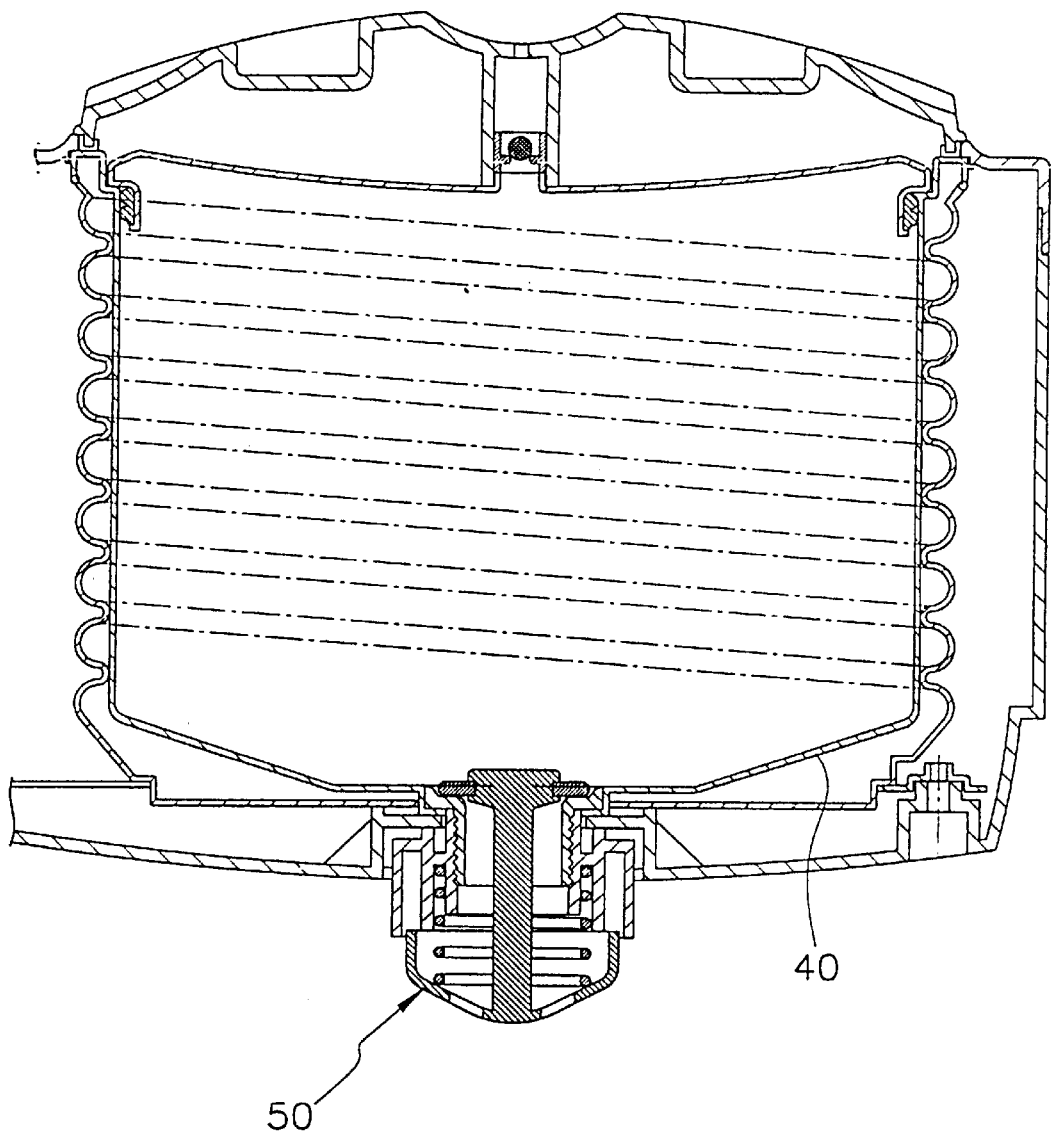
FIG. 2 is an enlarged vertical section of the heating vessel of the conventional decoctor.
Figure 3:
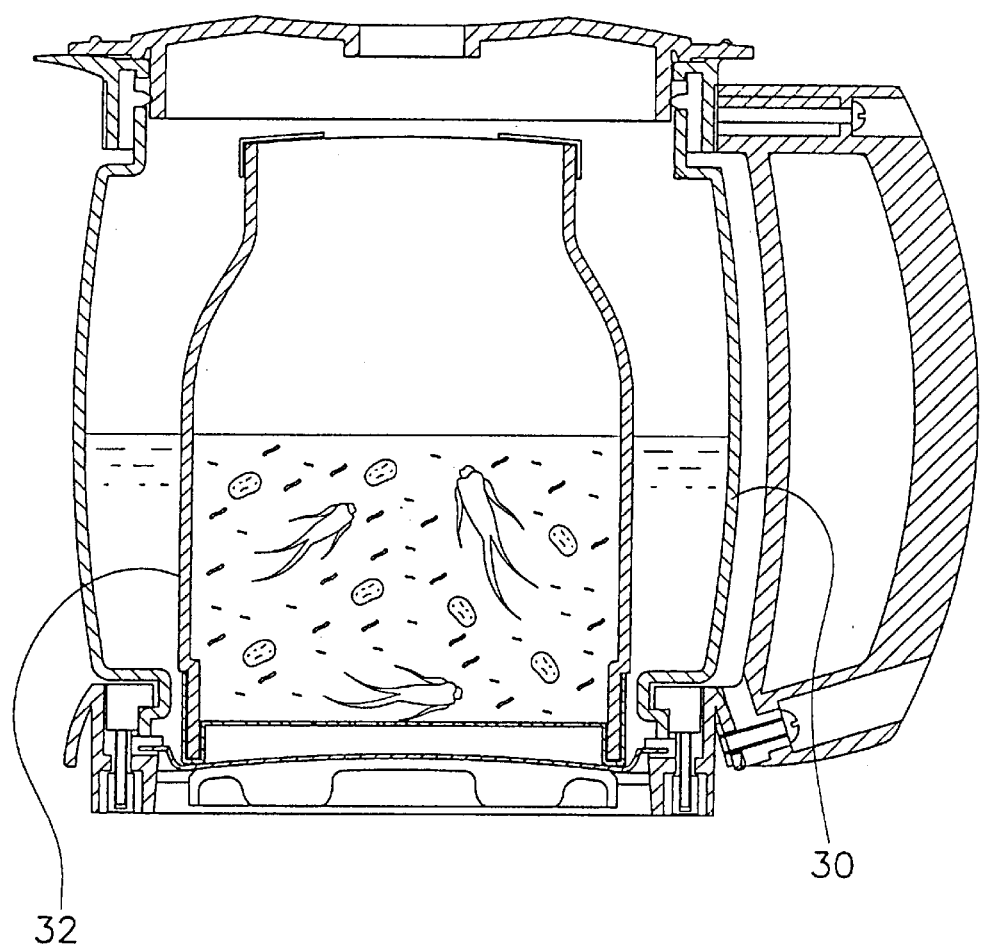
FIG. 3 is an enlarged vertical section of the steam condensing means of the decoctor.
Figure 4:
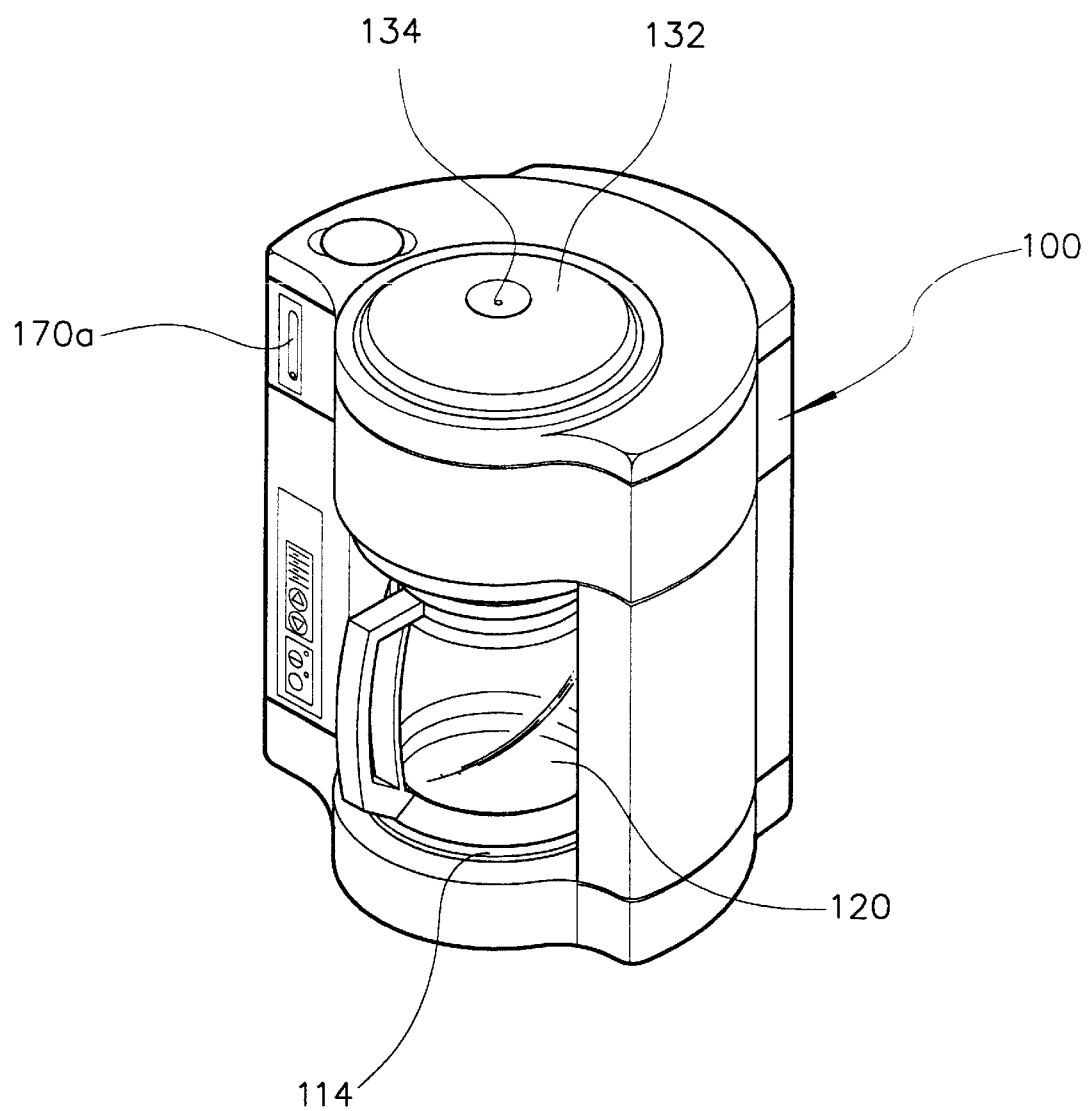
FIG. 4 is an assembled perspective of an embodiment of a home-style decoctor of the present invention.
Figure 5:
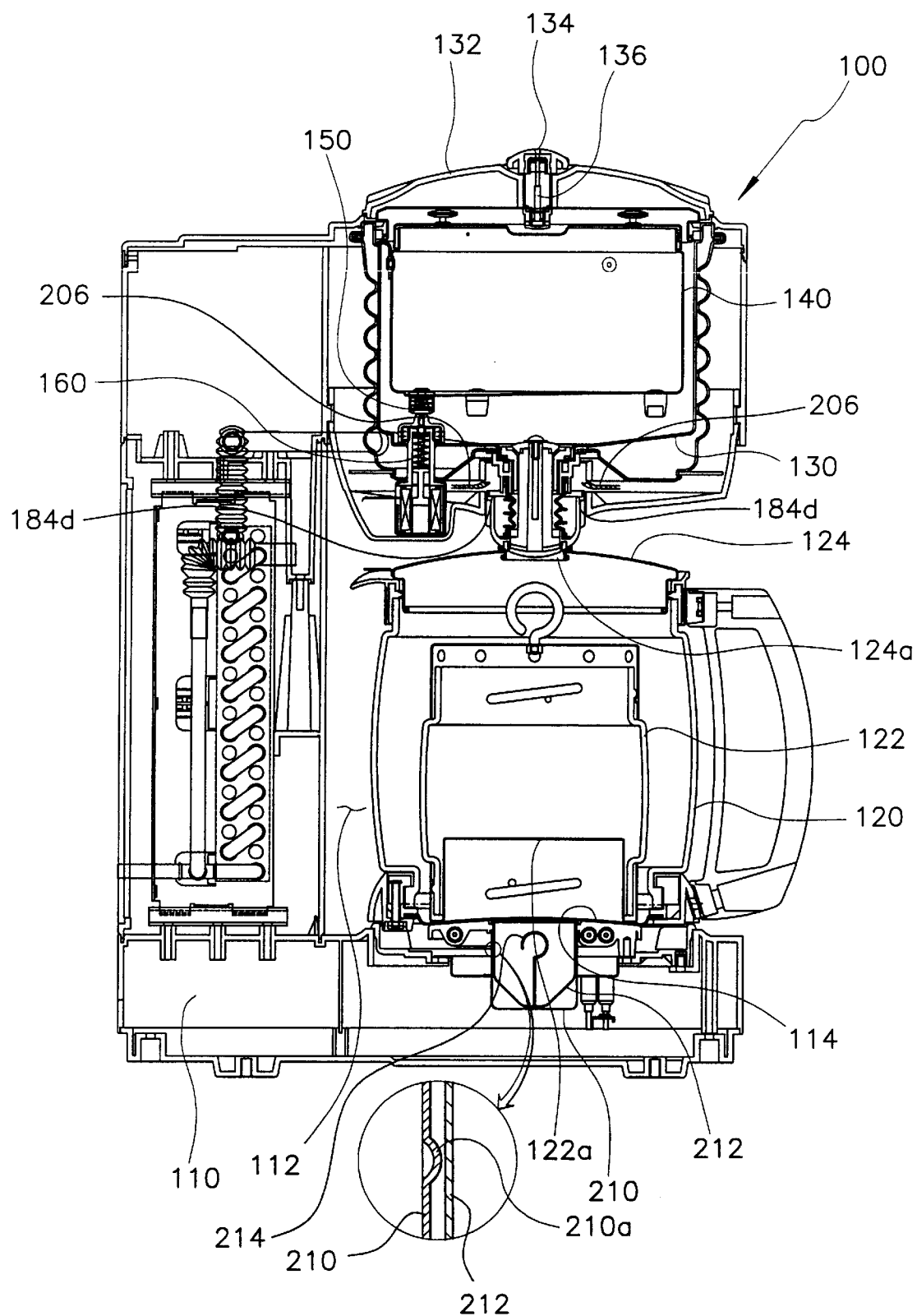
FIG. 5 is a vertical section of the decoctor of the present invention.
Figure 6:
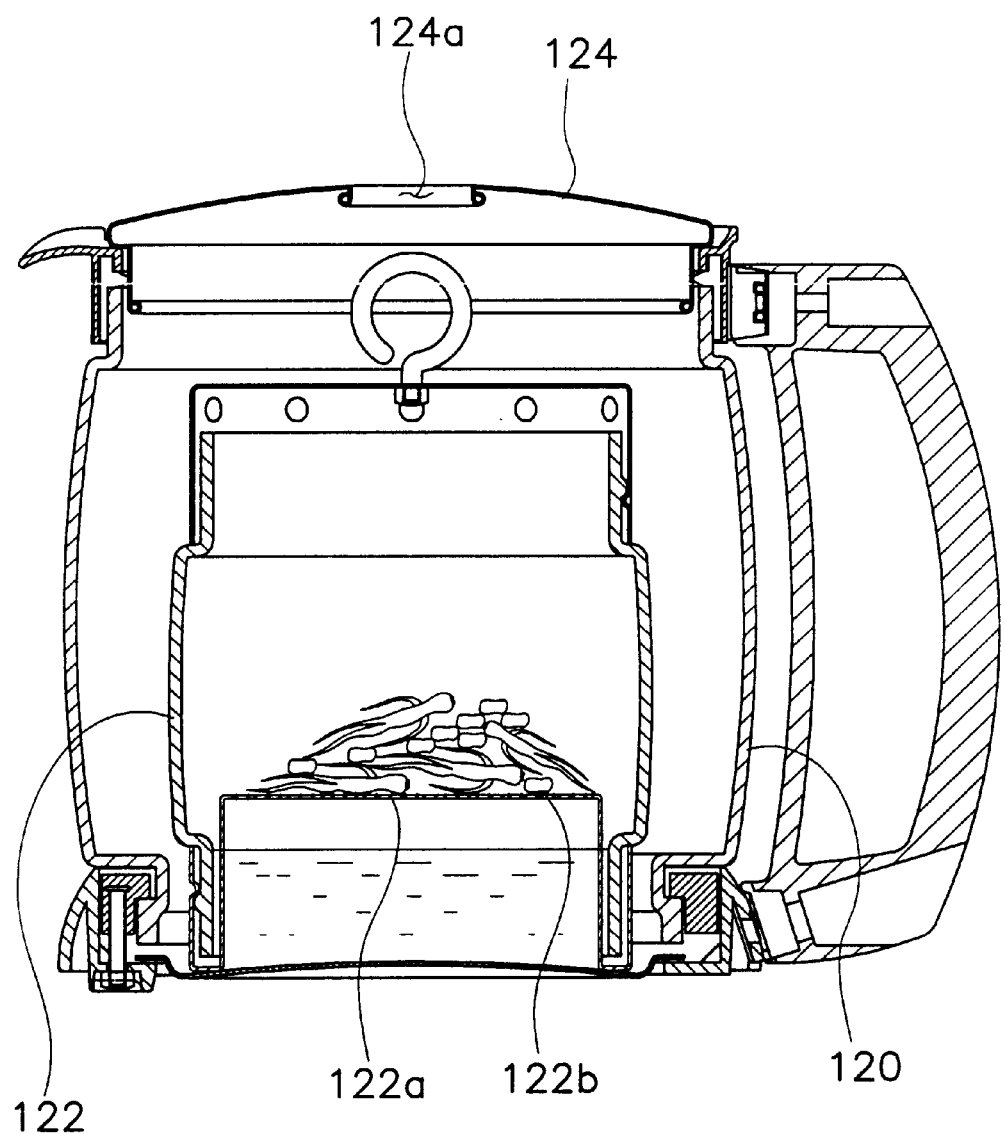
FIG. 6 is an enlarged vertical section of the heating vessel of the decoctor of the present invention.
Figure 7:
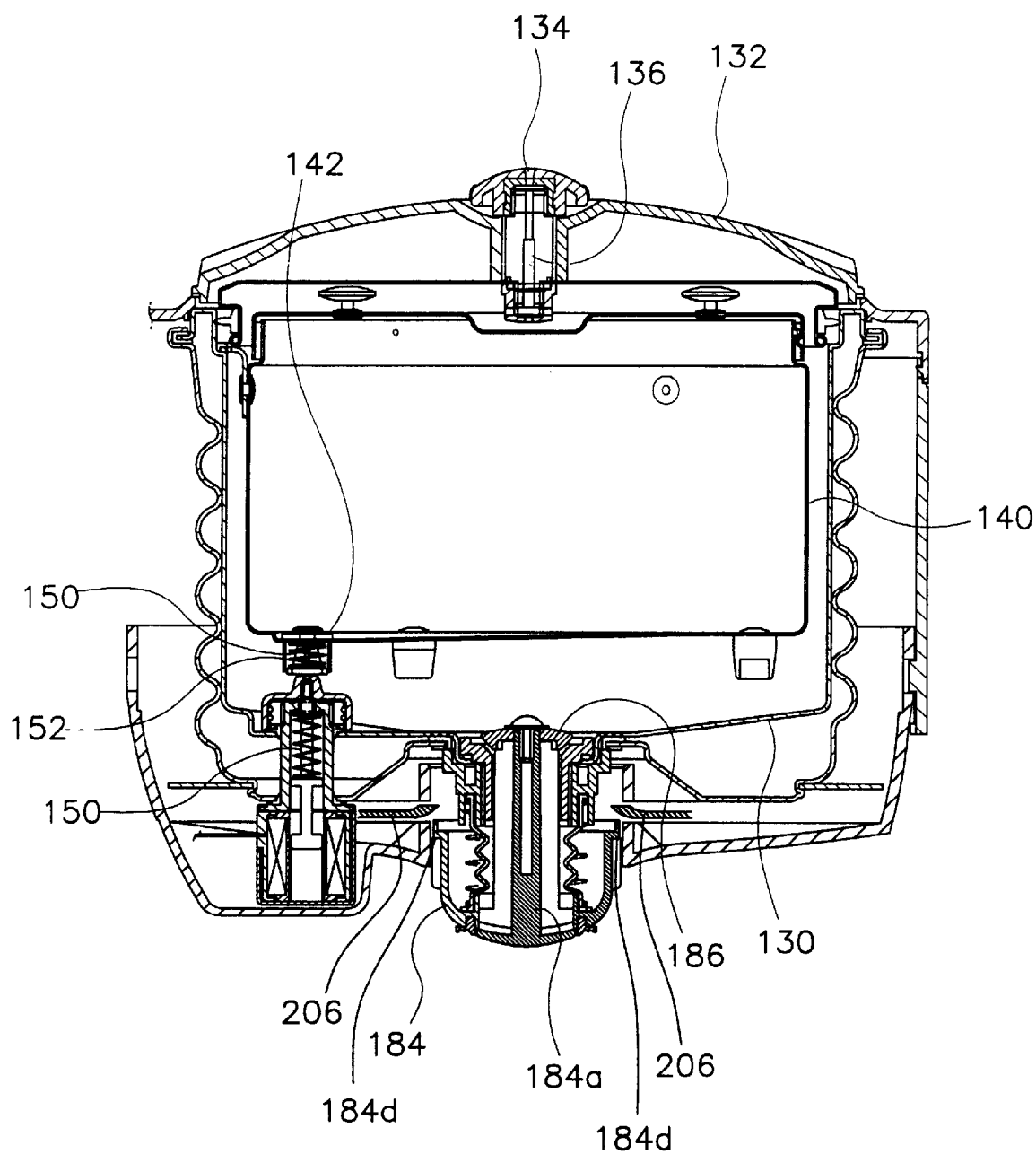
FIG. 7 is an enlarged vertical section of the steam collector of the decoctor of the present invention.

Referring to FIGS. 4, 5 and 6, a home-style decoctor 100 of the present invention comprises: a main body 110 equipped with a heater 114 at an appropriate place of its bottom; a heating vessel 120 for containing and heating a predetermined amount of water; a support plate 122a built in heating vessel 120, the plate having a plurality of throughholes 122b and for supporting a to-be-boiled object when it is steam-boiled; a steam collector 130 for gathering steam produced when heating vessel 120 is heated; means for condensing the steam collected into steam collector 130; and steam/condensed water guiding means for leading the steam present in heating vessel 120 to steam collector 130 and the condensed water placed in steam collector 130 to heating vessel 120.

In the above-explained construction, when heating vessel 120 having therein a to-be-boiled object is heated, the object being supported with support plate 122a so as not to be sunk into water, it is boiled with the steam generated. After the steam boiling of the object for a predetermined time, power is turned off to dry it, and a predetermined amount of water is gathered into heating vessel 120 so that the object steam-boiled and dried is sufficiently sunk into water. In this state, heating vessel 120 is heated to boil water and the object.

Here, after the steam boiling and drying, a predetermined amount of water for boiling is manually poured into heating vessel 120 which is separated from main body 110 so high that the object is immersed.

When undried or white ginseng is steam-boiled, dried and then boiled with the decoctor 100 of the present invention, useful components contained in red ginseng made when undried ginseng is steam-boiled and dried may be produced.

A method of preparing red ginseng extract using the home-style decoctor 100 of the invention comprises the steps of: safely placing in heating vessel 120 support plate 122a equipped with a plurality of throughholes 122b and having ginseng (undried or white) thereon, and then gathering water so high that the ginseng is not immersed; steam-boiling the ginseng for a predetermined time with the steam produced when heating vessel 120 is heated; drying the ginseng for a predetermined time while heater 114's power is off; gathering water for boiling in heating vessel 120 so high that the steam-boiled and dried ginseng is immersed; and boiling heating vessel 120 for a predetermined time while the steam-boiled and dried ginseng contained in heating vessel 120 is drowned in the incoming water.

More specifically, after support plate 122a is stably placed in heating vessel 120 and ginseng is put on support plate 122a, a predetermined amount of water is poured so high that the ginseng is not immersed. Then, the water is heated to enable the ginseng to be boiled with steam.

When the steam boiling of ginseng is performed for a predetermined time, heater 114's power is turned off to thereby dry the ginseng. Water for boiling is poured into heating vessel 120 so high that the steam-boiled and dried ginseng is drowned. Through this procedure of re-heating, the ginseng is boiled in water.

With such processes of steam boiling, drying and re-boiling, ginseng bears several kinds of phenolic compounds and maltol, which are contained in red ginseng as the aging-resistants (anti-oxidants), and ginsenosides Rg and Rh. During the steam boiling of ginseng, there are generated such components as several kinds of phenolic compounds and maltol included in red ginseng as the aging resistants (anti-oxidants). During the re-boiling process ginsenosides Rg and Rh are produced. Therefore, several kinds of phenolic compounds and maltol, the aging resistants (anti-oxidants), and ginsenosides Rg and Rh, all of which are produced during the steam boiling, drying and re-boiling, are drawn out to become red ginseng extract.

From now on, home-style decoctor 100 of the invention is explained in more detail. Referring to FIGS. 4 to 11, home-style decoctor 100 comprises: a main body 110 equipped with a heater 114 at an appropriate place of its bottom; a heating vessel 120 for containing and heating a predetermined amount of water; an inner vessel 122 safely positioned in heating vessel 120 for supporting a to-be-boiled object with its inner support plate 122a; a steam collector 130 for gathering steam produced when heating vessel 120 is heated; a water-for-boiling tank 140 installed on the inner side of steam collector 130 for storing water; an open/close valve 150 for discharging water for boiling stored in water-for-boiling tank 140 into steam collector 130; a solenoid 160 for opening or closing open/close valve 150 under control; means for condensing the steam collected into steam collector 130; and steam/condensed water guiding means for leading the steam present in heating vessel 120 to steam collector 130 and the condensed water placed in steam collector 130 to heating vessel 120.

In the above-explained construction, when a to-be-boiled object contained in heating vessel 120 is not sunk into water but heating vessel 120 is heated, the object is boiled with the steam generated. After the steam boiling of the object for a predetermined time, power is turned off to dry it, and a predetermined amount of water is gathered into heating vessel 120 so that the object steam-boiled and dried is sufficiently immersed into water. In this state, heating vessel 120 is heated to boil water and the object.

For more detailed description of the construction of the invention, the connection and operation of components will be recited below. First of all, main body 110 constitutes the exterior of home-style decoctor 100 endowed with steamy boiling function of the invention. The decoctor's components are installed inside or at appropriate places of main body 110. Especially, heater 114 for heating the heating vessel 120 is installed under a heating vessel receiver 112 provided on the front of main body 110 for accepting heating vessel 120. In the upper part of main body 110, steam collector 130 and components related thereto are provided.

Heating vessel 120 acts to heat a predetermined amount of stored water by means of heater 114. By doing so, steam is generated in the heating vessel 120.

The inner vessel 122 enables an object boiled to be positioned therein. On the bottom of inner vessel 122, support plate 122a equipped with a plurality of throughholes 122b is positioned so that the to-be-boiled object is placed above the surface of water stored in heating vessel 120. Thus constructed inner vessel 122 is safely placed in heating vessel 120 while the to-be-boiled object is positioned on support plate 122a.

The reason why the to-be-boiled object is designed to be positioned above the surface of water stored in heating vessel 120 is to perform steamy boiling which is aimed by the invention. The invention's purpose is accomplished by positioning the to-be-boiled object above water stored by means of support plate 122a of inner vessel 122.

When the to-be-boiled object is put on support plate 122a of inner vessel 122 which is then safely placed in heating vessel 120, the object put on support plate 122a is placed higher than the surface of water stored in heating vessel 120 so that the object is not immersed into water stored in heating vessel 120. Here, when steam is produced with heating vessel 120 heated, the steam rises through a plurality of throughholes 122b formed on support plate 122a so that the object put on support plate 122a is steam-boiled. Meanwhile, the steam raised is gathered into steam collector 130 by means of the steam/condensed water guiding means.

The steam collector 130 is designed to gather steam produced when heating vessel 120 is heated. The vessel is installed in the upper part of main body 110, and communicates with heating vessel 120 by means of the steam/condensed water guiding means. The steam collected into steam collector 130 is cooled and condensed by the steam condensing means. Here, a lid 132 for covering steam collector 130 has a steam discharging valve 136 which opens to release steam through a steam discharging hole 134 when the internal pressure of steam collector 130 reaches a predetermined point due to the steam gathered into steam collector 130. The steam condensing means is recited later.

Water-for-boiling tank 140 is a container for storing water for boiling to be supplied into heating vessel when boiling for extracting the object's components is carried out after steamy boiling. The tank is installed on the inner side of steam collector 130. Here, the bottom of water-for-boiling tank 140 is designed to be separated from the inner bottom of steam collector 130 at a predetermined distance. In other words, there is a space between the bottom of water-for-boiling tank 140 installed on the inner side of steam collector 130 and the inner top of steam collector 130. Open/close valve 150 is installed on water-for-boiling tank 140 for drawing out water stored therein.

As described above, the open/close valve 150 acts to pour water stored in water-for-boiling tank 140 into steam collector 110. The valve is installed in discharging hole 142 formed on the bottom of water-for-boiling tank 140 for discharging water-for-boiling, and opens or closes by means of later-mentioned solenoid 160. When valve 150 opens, water stored in tank 140 enters steam collector 130 and then heating vessel 120 through steam/condensed water guiding means.

Solenoid 160 opens open/close valve 150 installed at an appropriate position of the bottom of water-for-boiling tank 140. The solenoid is installed at an appropriate place of the inner side of main body 110 and on the bottom of open/close valve 150. Thus installed solenoid 160 is operated according to a control signal to open valve 150 for a predetermined time. Valve 150 opens as long as water contained in water-for-boiling tank 140 is sufficiently drawn out.

After water stored in tank 140 sufficiently goes into steam collector 130 with open/close valve 150 being opened and when the control signal is off, solenoid 160 returns to the original position and open/close valve 150 also does due to the resilient force of spring 152.

Figure 8:
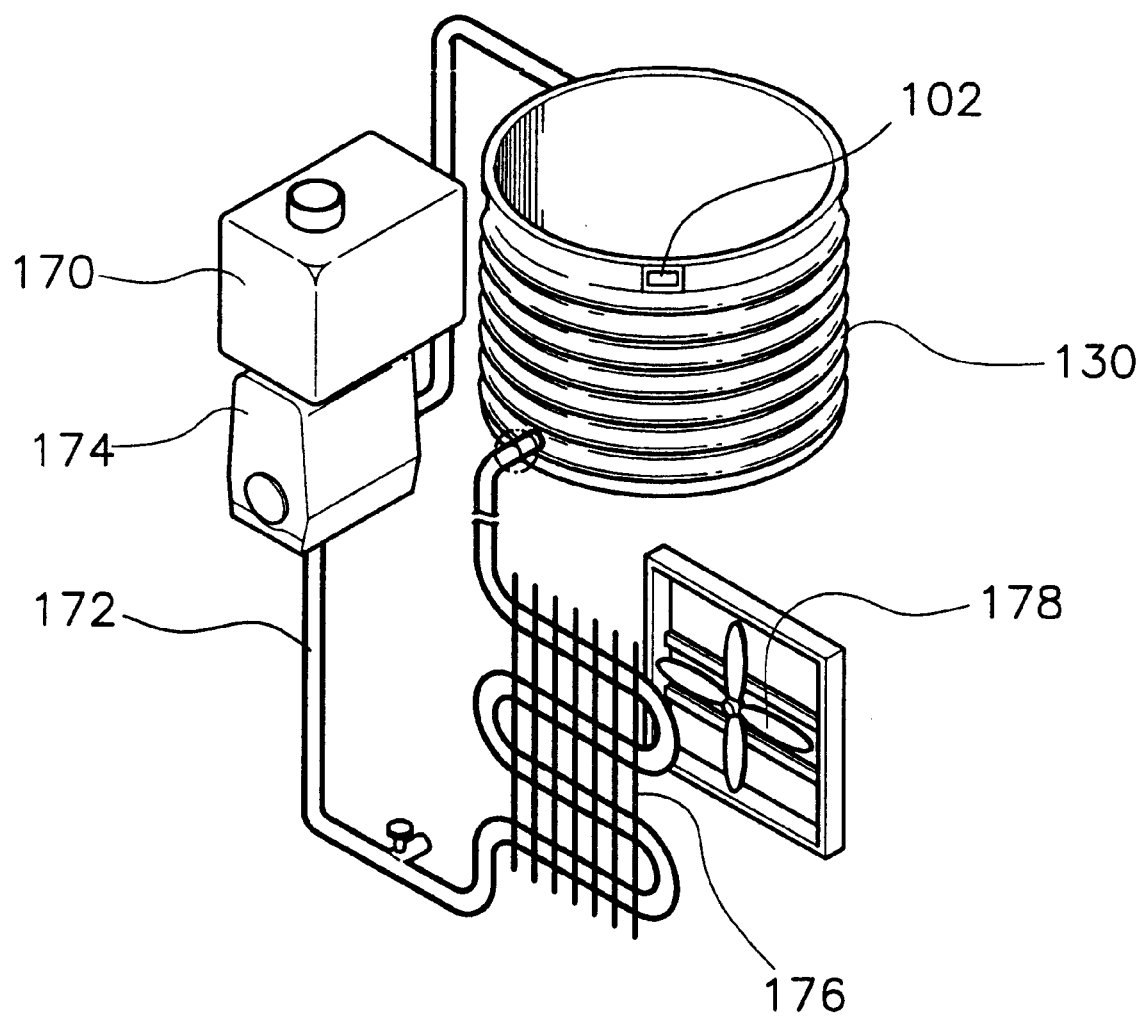
FIG. 8 is a perspective of the steam condensing means of the decoctor of the invention.

The steam condensing means cools and condenses the steam gathered into steam collector 130, the means comprising a cooling water reservoir 170, a cooling water circulation tube 172, a cooling water circulation pump 174, and a heat-resistant pin 176, as shown in FIG. 8.

Cooling water reservoir 170 stores cooling water for cooling steam collector 130 whose temperature is raised due to steam, the reservoir being installed at an appropriate position of the top of main body 110.

Cooling water circulation tube 172 cools steam collector 130 by circulating the cooling water stored in cooling water reservoir 170 around the collector 130. The cooling water circulation tube 172 is installed on the circumference of steam collector 130 in the spiral form, circulating cooling water toward the exit through the entrance.

Cooling water circulation pump 174 forcibly circulates the cooling water contained in cooling water reservoir 170. When cooling water circulation pump 174 is driven, the cooling water stored in cooling water reservoir 170 enters cooling water circulation tube 172 via the entrance, spirally circulates steam collector 130, and then goes into cooling water reservoir via the exit. When cooling water circulation pump 174 is continuously driven, the cooling water stored in cooling water reservoir 170 also ceaselessly circulates steam collector 130 to cool it.

Heat-resistant pin 176 cools the cooling water whose temperature is raised because it circulates steam collector 130 to cool it. This pin is installed on cooling water circulation tube 172 to cool cooling water circulation tube 172 and thus lower the temperature of the cooling water circulated, by externally radiating heat received from cooling water circulation tube 172.

In audition to the construction of the steam condensing means, a cooling water residual indicator 170a is provided at an appropriate place of one side of main body 110 for confirming the residual of cooling water contained in cooling water reservoir 170. A cooling fan 178 is disposed at an appropriate position near heat-resistant pin 176 inside main body 110, the fan cooling heat-resistant pin 176. The fan 178 cools heat-resistant pin 176 more quickly through ventilation, decreasing more rapidly the temperatures of cooling water circulation tube 172 and cooling water.

The home-style decoctor 100 of the invention further comprises means for detecting the temperatures of steam collector 130 and cooling water circulation tube 172 if cooling water circulation pump 174 or cooling fan 178 has a problem, deciding that there occurs trouble therein if the temperatures reach a predetermined point, and thus turning off heater 114 to thereby prevent its overheating.

For the overheating preventive means of the decoctor 100, there is provided a temperature sensor 102 for detecting the temperature of steam collector 130 at an appropriate position of one side thereof. The overheating preventive means equipped with temperature sensor 102 measures the temperature of steam collector 130, compares it with a predetermined temperature, and, if the temperature of steam collector 130 rises above a predetermined point, decides that cooling water circulation pump 174 or cooling fan 178 has a problem, to thereby turn off the output of heater 114.

Figure 9:
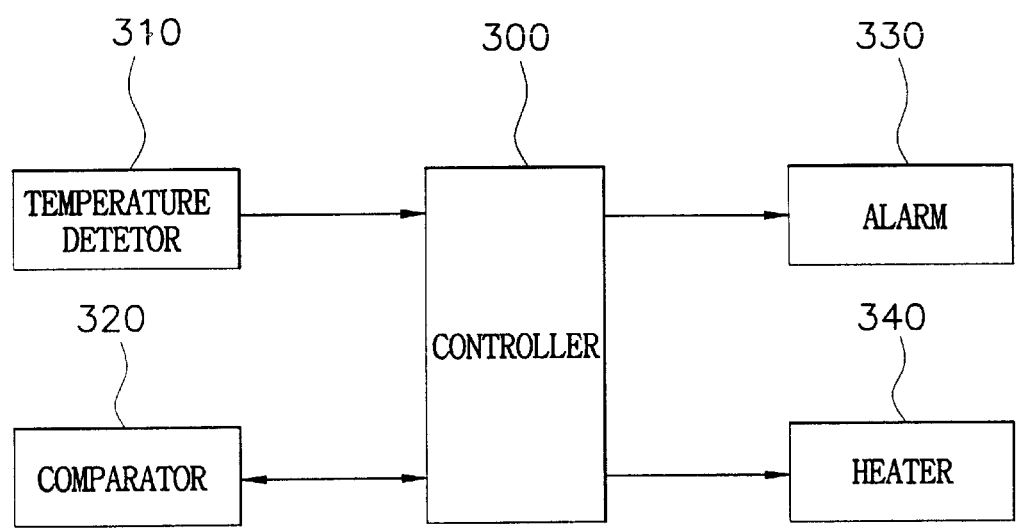
FIG. 9 is a block diagram of the overheating preventive device of the decoctor of the invention.

More specifically, as shown in FIGS. 8 and 9, the overheating preventive means of decoctor 100 comprises: a temperature detecting portion 310 installed on one side of steam collector 130 for detecting the temperature of steam collector 130; a comparing portion 320 for comparing the temperature of steam collector 130 detected by temperature detecting portion 310 with a predetermined point; a controller 300 for, if the temperature of steam collector 130 goes above a predetermined point, deciding that cooling water circulation pump 174 or cooling fan 178 has a problem to thereby turn off the power of heater 114, the controller further controlling the general operations of decoctor 100; and an alarm 330 for generating an alarm which can be recognized by an user when it is decided by controller 300 that cooling water circulation pump 174 or cooling fan 178 has trouble.

The operation of the above-explained overheating preventive means is described below. Temperature detecting portion 310 measures the temperatures of steam collector 130 and cooling water circulation tube 172, the measured values being sent to controller 300. The temperature values received in controller 300 are compared with a predetermined value in comparing portion 320, the compared result being transmitted to controller 300.

According to the result sent to controller 300 from comparing portion 320, if the temperature values measured in steam collector 130 and cooling water circulation tube 172 are greater than a predetermined value, controller 300 turns off the power of heater 340 and then generates-an alarm which can be recognized aurally and visually by an user. Here, for means of producing alarm, a buzzer is employed as aural means, and an on-and-off light as visual means. Only a buzzer or both of a buzzer and on-and-off light may be provided.

Figure 10:
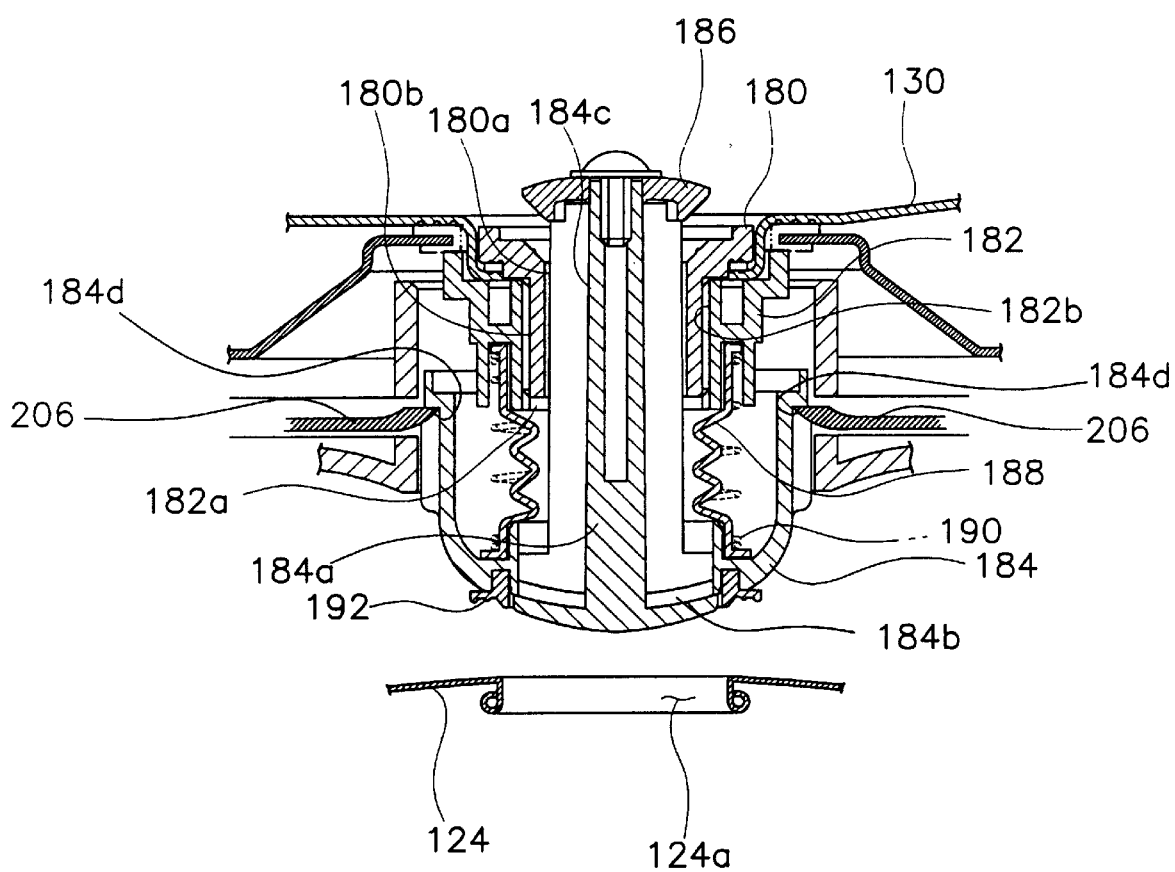
FIG. 10 is a vertical section of the steam condensing means and heating vessel before assembled by the steam/condensed water guiding means.
Figure 11:
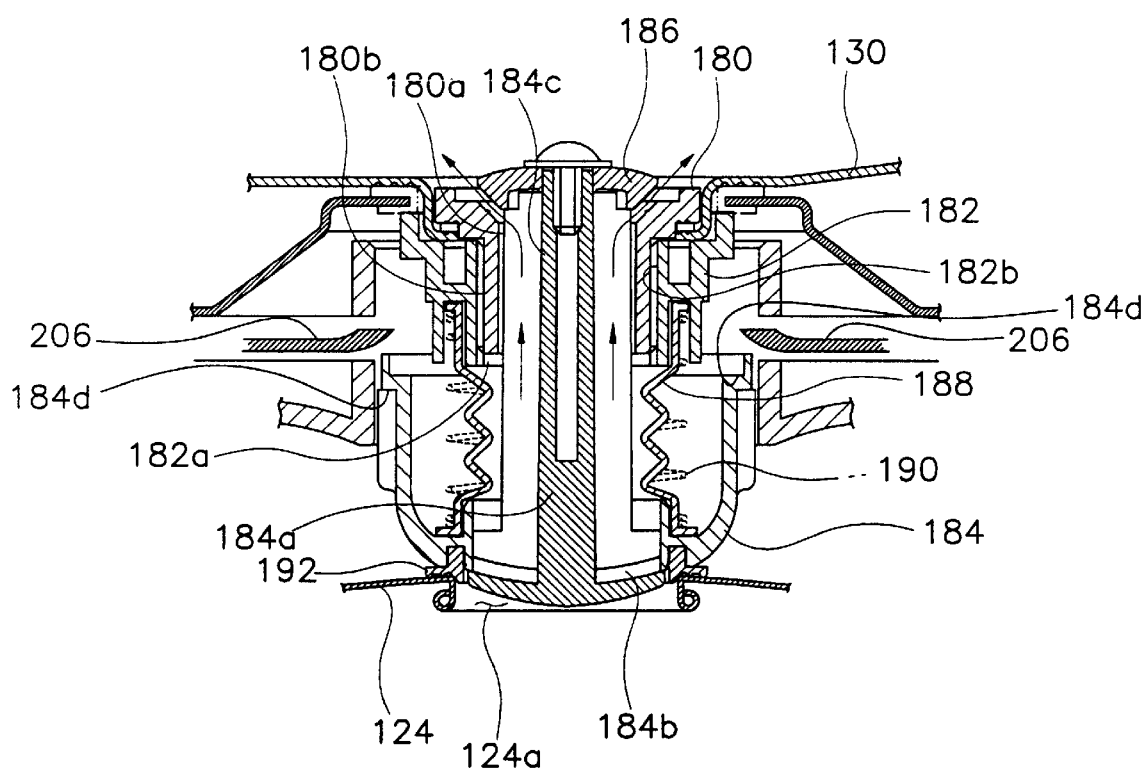
FIG. 11 is a vertical section of the steam condensing means and heating vessel after assembled by the steam/condensed water guiding means.

As described above, the overheating of decoctor 100 can be prevented by turning off the power of heater 114 when the temperature of steam collector 130 or cooling water circulation tube 172 is raised above a predetermined point and it is thus determined that cooling water circulation pump 174 or cooling fan 178 has a problem. Turning to FIGS. 5, 10 and 11, the steam/condensed water guiding means leads the steam contained in heating vessel 120 and produced when it is heated, into steam collector 130, and the condensed water made in steam collector 130 into heating vessel 120. This means comprises: upper and lower support members 180 and 182 vertically and respectively having steam guiding holes 180a and 182a at their centers and screw-fastened with the bottom of steam collector 130 being interposed; a steam guiding portion 184 which communicates with steam hole 124a formed in heating vessel lid 124, the portion for leading the steam contained in heating vessel 120 to steam collector 130 and the condensed water stored in steam collector 130 to heating vessel 120; a support shaft 184a vertically formed at an appropriate position inside steam guiding portion 184 and vertically and movably inserted into steam guiding holes 180a and 182a of upper and lower support members 180 and 182; an open/close member 186 fastened at the top of support shaft 184a for opening or closing the top of the steam guiding hole of upper support member 180 and allowing steam guiding portion 184 and support shaft 184a to be supported by upper and lower support members 180 and 182 when steam guiding portion 184 moves up and down; an elastic wavy tube 188 installed on the circumference of support shaft 184a and whose top and bottom surfaces come into tight contact with the bottom of lower support member 182 and the inner top of steam guiding portion 184, respectively, the tube for leading the steam contained in heating vessel 120 to steam collector 130 and the condensed water stored in steam collector 130 to heating vessel 120 through steam guiding portion 184; and a resilient spring 190 installed at the circumference of wavy tube 188 for allowing the top and bottom of wavy tube 188 to come into close contact with the bottom of lower support member 182 and the inner top of steam guiding portion 184, the spring executing its force to enable steam guiding portion 184 usually to return to the original position.

In more detail, upper support member 180 is formed vertically with steam guiding hole 180a at its center. In the lower part of support member 180 a male screw 180b is formed so that the support member passes from the inner center to the outer bottom of the steam collector 130.

Lower support member 182 has steam guiding hole 182a vertically penetrated in relation to steam guiding hole 180a of upper support member 180. A female screw 182b is formed on the inner circumference of steam guiding hole 182a in relation to male screw 180b of upper support member 180. With the male and female screws, the lower support member is fastened with upper support member 180 at the bottom of steam collector 130. Steam guiding holes 180a and 182a of respective members 180 and 182 communicate vertically due to the vertical fastening between upper and lower support members 180 and 182 interposed with the bottom of steam collector 130. In other words, the lower center of steam collector 130 is open through respective steam guiding holes 180a and 182a of upper and lower support members 180 and 182.

Steam guiding portion 184 leads the steam of heating vessel 120 to steam collector 130 through steam guiding hole 182a of lower support member 182 and the condensed water of steam collector 130 to heating vessel 120. The steam guiding portion leads the steam or condensed water through steam guiding hole 184b making a sheet-contact with steam hole 124a formed in the heating vessel lid 124 and thus vertically penetrated therewith. The steam guiding portion 184 is positioned under lower support member 182 while propped up by support shaft 184a vertically formed on the inner top of the portion and by open/close member 186 fastened to the top of support shaft 184a.

Formed vertically on the inner top surface of steam guiding portion 184, support shaft 184a is penetratingly inserted into respective steam guiding holes 180a and 182a of upper and lower support members 180 and 182 so that steam guiding portion 184 is designed to move vertically only along the center line of steam guiding holes 180a and 182a for a predetermined distance. Depending upon the presence or absence of heating vessel 120, steam guiding portion 184 moves vertically along respective steam guiding holes 180a and 182a of upper and lower support members 180 and 182, and is thus guided vertically only along the center line of steam guiding holes 180a and 182a.

Along the lengthwise circumference of support shaft 184a, a plurality of guiding pieces 184c are formed at predetermined intervals so that the support shaft 184a is guided only vertically in steam guiding holes 180a and 182a of upper and lower support members 180 and 182. Here, the steam of heating vessel 120 and the condensed water of steam collector 130 pass between guiding pieces 184c of support shaft 184a.

Open/close member 186 is fastened to the top of support shaft 184a penetrating through respective steam guiding holes 180a and 182a of upper and lower support members 180 and 182 and protruded from the top of steam guiding hole 180a of upper support member 180. Made of resilient deformable synthetic resin, the open/close member enables steam guiding portion 184 and support shaft 184a to be supported by upper and lower support members 180 and 182. Especially, rubber is favorable for the member 186.

In addition to the function of allowing steam guiding portion 184 and support shaft 184a to be supported by upper and lower support members 180 and 182, open/close member 186 has a function of opening or closing the top of steam guiding hole 180a of upper support member 180 according to the presence or absence of heating vessel 120. Specifically, open/close member 186 opens or closes steam guiding hole 180a placed on the top of upper support member 180 according to the vertical movement of steam guiding portion 184, the movement depending upon the presence or absence of heating vessel 120.

The opening of the top of steam guiding hole 180a of upper support member 180 means that the steam of heating vessel 120 goes into steam collector 130 and the condensed water of steam collector 130 into heating vessel 120. When the top of steam guiding hole 180a of upper support member 180 is closed, steam or condensed water cannot be guided therethrough.

When support shaft 184a penetrates respective steam guiding holes 180a and 182a of upper and lower support members 180 and 182 and open/close member 186 is fastened to the top of support shaft 184*a* protruded from the top of steam guiding hole 180*a* of upper support member 180, support shaft 184*a* placed between open/close member 180 and steam guiding portion 184 is longer than respective steam guiding holes 180*a* and 182*a* of upper and lower support members 180 and 182 so that support shaft 184*a* moves vertically by the difference. In other words, steam guiding portion 184 can move by the difference between the length of support shaft 184*a* placed between open/close member 186 and steam guiding portion 184, and the length of upper and lower support member 180 and 182 and steam guiding holes 180*a* and 182*a*.

Wavy tube 188 is designed to prevent the external steam leakage possibly occurring when the steam of heating vessel 120 passes through steam guiding portion 184 of the steam/condensed water means and respective steam guiding holes 182*a* and 180*a* of upper and lower support members 182 and 180. In order to guide steam or condensed water, the wavy tube is installed on the outer circumference of support shaft 184*a*, the top and bottom end surfaces coming into close contact with the bottom of lower support member 182 and the inner top of steam guiding portion 184. Made of rubber of good elasticity, wavy tube 188 additionally acts to alleviate the reduction of the resilient force of below-explained spring 190.

Elastic spring 190 executes its force in the direction of returning steam guiding portion 184 to its original position. Therefore, when the force of raising steam guiding portion 184 disappears, it is made to instantly return to the original position. Installed on the circumference of wavy tube 188, spring 190 causes the top and bottom surfaces of wavy tube 188 to come into close contact with the bottom surface of lower support member 182 and the inner top surface of steam guiding portion 184. In addition, the spring always executes its force to return steam guiding portion 184 to the original position. This allows the top surface of heating vessel lid 124 to come into close contact with the bottom surface of steam guiding portion 184.

In the construction of the steam/condensed water guiding means, a sealing member 192 in the form of concentric circle is further provided on the bottom of steam guiding portion 184, the member preventing the leakage of steam by tightening the border of steam hole 124*a* of heating vessel lid 124 and the bottom of steam guiding portion 184.

The wavy tube 188 and sealing member 192 of the steam/condensed guiding means prevents the steam leakage from the steam/condensed water guiding means and also between heating vessel lid 124 and the bottom of steam guiding hole 184*b* when steam hole 124*a* of heating vessel lid 124 coincides with steam guiding hole 184*b* of steam guiding portion 184 and thus the borders of steam hole 124*a* and steam guiding hole 184*b* are tightened by means of sealing member 192 while heating vessel 120 is safely placed in heater 114.

From now on, the operation of steam/condensed water guiding means is described. First of all, when heating vessel 120 is put into heater 114 of main body 110 and the steam guiding hole of steam guiding portion 184 coincides with steam hole 124*a* formed in the center of heating vessel lid 124, steam guiding portion 184 moves up and then the top of steam guiding hole 180*a* of upper support member 180 is opened so that the steam of heating vessel 120 can go into steam collector 130 through respective steam guiding holes 184*b*, 182*a* and 180*a* of steam guiding portion 184, lower support member 182 and upper support member 180. This state indicates that the condensed water of steam collector 130 reversely falls down into heating vessel 120 through the steam guiding portion.

If heating vessel 120 is detached from heater 114, then the force to push upward steam guiding portion 184 disappears so that it instantly returns to the original position due to the resilient force of wavy tube 188 and elastic spring 190. Here, steam guiding hole 180*a* of upper support member 180 is closed by means of open/close member 186.

Referring to FIGS. 5, 10 to 13*b*, main body 110 of decoctor 100 further comprises means for arresting the up and down movement of steam guiding portion 184. This steam guiding portion movement arresting means comprises: a stop 184*d* formed on the circumference of the steam guiding portion; a pushing member 200 one end of which is protruded outward from main body 110, the member rectilinearly and horizontally moving; a spring 202 whose force is executed to enable pushing member 200 always to be protruded outward; and an arresting member 206 installed to be rotable inward and outward horizontally at an appropriate position and on both sides in main body 110, one end of the member being coupled on hinge 204 with the other end of pushing member 200, the member moving inward and outward while engaging with pushing member 200 which moves horizontally, to be thereby caught or released from stop 184*d* of steam guiding portion 184.

The steam guiding portion movement arresting means is constructed that arresting member 206 is hinged at both ends of pushing member 200 placed inside main body, the member being rotable by rotation shaft 208. Here, when the force of pushing member 200 which is resiliently supported by spring 202 is removed, pushing member 200 and arresting member 206 always return to the original position. In this construction, the arresting means holds the up and down movement of steam guiding portion 184 when the free end of arresting member 206 rotates centering on rotation shaft 208 according to pushing member 200 to catch or release stop 184*d* of steam guiding portion 184.

In more detail, after heating vessel 120 is safely placed in heater 114 while stop 184*d* of steam guiding portion 184 is caught by arresting member 206, in other words, steam guiding portion 184 is moved up and held by arresting member 206, pushing member 200 is pressed to advance inward and thus arresting member 206 hinged on both inner ends of pushing member 200 rotates centering on rotation shaft 208 to release the free end of arresting member 206 and the stop 184*d*. Steam guiding portion 184 becomes free from arresting member 206 and thus moves down due to the resilient force of spring 190. As a result, the steam guiding portion is safely positioned in steam hole 124*a* of heating vessel lid 124.

Meanwhile, when heating vessel 120 is raised while steam guiding portion 184 is safely positioned in steam hole 124*a* of lid 124, steam guiding portion 184 moves up and thus stop 184*d* of steam guiding portion 184 is caught by the free end of arresting member 206. In this state steam guiding portion 184 is maintained to be moved up so that heating vessel 120 freely goes in or out.

As shown in FIG. 5, there is provided falling water receiver means placed at an appropriate position of heater 114 for withdrawing boiling solution falling from the steam/condensed guiding means when heating vessel 120 is detached from main body 110. This means comprises: an outer cask 210 installed at an appropriate place inside heater 114 on the central line of the steam/condensed guiding means; a falling water receiver 212 detachably installed on the inner side of outer cask 210 for collecting boiling solution falling from the steam/condensed water guiding means, and a handle 214 formed on the inner central bottom of falling water receiver 212 and used to allow barrel 212 to separate from outer cask 210. Here, the bottom of barrel 212 is formed conically to minimize the heat transmission from outer cask 210.

The thus constructed falling water receiver means withdraws residual boiling solution remaining and dropping from the inner side surf ace of wavy tube 188 of steam/condensed water guiding means when heating vessel 120 is detached from heater 114 after the boiling, to thereby prevent it f from being contaminated. The boiling solution collected from barrel 212 can be removed by separating it from outer cask 210 by means of handle 214.

In the construction of the falling water receiver means, there is further provided a plurality of contact preventive bumps 210a protuberantly formed on the inner side of outer cask 210 for causing the outer circumference of barrel 212 to come into no sheet-contact with the inner circumference of outer cask 210 when barrel 212 is safely positioned in the outer cask.

The contact preventive bumps 210a hinders the contact between falling water receiver 212 and outer cask 210, to thereby minimize the heat transmission from outer cask 210.

The home-style decoctor 100 of the present invention can be summarized as follows. As shown in FIGS. 4–13b, decoctor 100 is comprised of: a main body 110 of a predetermined size equipped with a heater 114 at an appropriate position of the bottom; a heating vessel 120 for containing and heating a predetermined amount of water with heater 114; a support plate 122a having a plurality of throughholes 122b and for allowing an object to be placed above the surface of water stored in heating vessel 120 and to be steam-boiled with the steam produced inside heating vessel 120; a steam collector 130 for gathering steam produced when the object is decocted with water for boiling poured in heating vessel 120 so high as to cause the object to be immersed after its steamy boiling and drying; means for condensing the steam collected into steam collector 130; and steam/condensed water guiding means for causing heating vessel 120 to communicate with steam collector 130 when the heating vessel is safely placed in main body 110 and thus leading the steam present in heating vessel 120 to steam collector 130 and the condensed water placed in steam collector 130 to heating vessel 120.

In the above construction there is further provided means in main body 110 of decoctor 100 for supplying water for boiling into heating vessel 120 so high as to cause the to-be-boiled object to be immersed after its steamy boiling and drying. This means comprises: a water for boiling tank 140 installed to be spaced apart upward from the inner bottom of steam-collector 130 for storing so much an amount as to cause the to-be-boiled object contained in heating vessel 120 to be immersed; an open/close valve 150 installed at an appropriate position of the bottom of tank 140 for discharging water for boiling into steam collector 130 according to the opening/closing action; and a solenoid 160 installed at an appropriate position of main body 110 placed under open/close valve 150 for opening or closing open/close valve 150.

Another embodiment of decoctor 100 of the present invention is comprised of: a main body 110 of a predetermined size equipped with a heater 114 at an appropriate position of the bottom; a heating vessel 120 for containing and heating a predetermined amount of water with heater 114; an inner vessel 122 having a support plate 122a equipped with a plurality of throughholes 122b for allowing an object to be placed above the surface of water stored in heating vessel 120, the vessel causing the object to be steam-boiled with the steam produced inside heating vessel 120; a steam collector 130 installed in the upper portion of main body 110 and for gathering steam produced when the object is decocted; a water for boiling tank 140 installed to be spaced apart upward from the inner bottom of steam collector 130 for storing so much an amount as to cause the to-be-boiled object contained in heating vessel 120 to be immersed; an open/close valve 150 installed at an appropriate position of the bottom of tank 140 for discharging water for boiling into steam collector 130 according to the opening/closing action; a solenoid 160 installed at an appropriate position of main body 110 placed under open/close valve 150 for opening or closing open/close valve 150; means for condensing the steam collected into steam collector 130; and steam/condensed water guiding means for causing heating vessel 120 to communicate with steam collector 130 when the heating vessel is safely placed in main body 110 and thus leading the steam present in heating vessel 120 to steam collector 130 and the condensed water placed in steam collector 130 to heating vessel 120.

The steam condensing means comprises: a cooling water reservoir 170 installed at an appropriate position of main body 110 for storing cooling water; a cooling water circulation tube 172 installed spirally on the circumference of steam collector 130 for allowing the cooling water stored in cooling water reservoir 170 to flow; a cooling water circulation pump 174 for forcibly circulating the cooling water stored in cooling water reservoir 170 into cooling water circulation tube 172; and a heat-resistant pin 176 installed at an appropriate place of cooling water circulation tube 172 for radiating heat of the cooling water whose temperature is raised. In addition there is installed a cooling fan 178 installed at an appropriate place of main body 110 near heat-resistant pin 176 for cooling it.

The steam/condensed water guiding means comprises: upper and lower support members 180 and 182 vertically and respectively having steam guiding holes 180a and 182a at their centers and screw-fastened with the bottom of steam collector 130 being interposed; a steam guiding portion 184 which communications with steam hole 124a formed in heating vessel lid 124, the portion for leading the steam contained in heating vessel 120 to steam collector 130 and the condensed water stored in steam collector 130 to heating vessel 120; a support shaft 184a vertically formed at an appropriate position inside steam guiding portion 184 and vertically and movably inserted into steam guiding holes 180a and 182a of upper and lower support members 180 and 182; an open/close member 186 fastened at the top of support shaft 184a for opening or closing the top of the steam guiding hole of upper support member 180 and allowing steam guiding portion 184 and support shaft 184a to be supported by upper and lower support members 180 and 182 when steam guiding portion 184 moves up and down; an elastic wavy tube 188 installed on the circumference of support shaft 184a and whose top and bottom surfaces come into tight contact with the bottom of lower support member 182 and the inner top of steam guiding portion 184, respectively, the tube for leading the steam contained in heating vessel 120 to steam collector 130 and the condensed water stored in steam collector 130 to heating vessel 120 through steam guiding portion 184; and a resilient spring 190 installed at the circumference of wavy tube 188 for allowing the top and bottom of wavy tube 188 to come into close contact with the bottom of lower support member 182 and the inner top of steam guiding portion 184, the spring executing its force to enable steam guiding portion 184 usually to return to the original position. A sealing member 192 is further provided on the bottom of steam guiding portion 184, the member preventing the leakage of steam by tightening the border of steam hole 124a of heating vessel lid 124 and the bottom of steam guiding portion 184.

From now on, the steamy boiling and re-boiling with decoctor 100 of the invention are described. Above all, inner vessel 122 with a to-be-boiled object is safely placed in heating vessel 120, water is poured thereinto so high as not to cause the object on the inner vessel to be immersed, and thus the object and heating vessel 120 are heated with heater 114.

When steam is generated in heating vessel 120 heated, the steamy boiling of the object is performed by means of the steam generated. While continuously boiling the object, the steam enters steam collector 130 through the steam/condensed water guiding means. Here, the steam going into steam collector 130 is condensed by means of the steam condensing means and is then withdrawn into heating vessel 120 through the steam/condensed water guiding means. In other words, the steamy boiling of object is carried out while heating vessel 120 is heated for a predetermined time, and water therein is repeatedly circulated between heating vessel 120 and steam collector 130 in the form of steam or condensed water.

After the object is steam-boiled for a predetermined time through the steamy boiling, the power of heater 114 is turned off to dry the object boiled.

The open/close valve 150 is opened under the control of solenoid 160 after the drying of object for a predetermined time so as to discharge water stored in tank 140 to steam collector 130, the water going into steam collector 130 enters the heating vessel through the steam/condensed water guiding means. Here, the water going into heating vessel 120 enables the object contained in heating vessel 120 to be sufficiently immersed.

In the state that water for boiling goes into heating vessel 120 to allow the object to be sufficiently immersed, heater 114 is turned on to thereby re-boil the contents (water and object to be boiled) of heating vessel 120. Here, the water in heating vessel 120 repeatedly circulates heating vessel 120 and steam collector 130 in the form of steam or condensed water, as in the process of steamy boiling. Through the re-boiling in heating vessel 120 heated for a predetermined time, components contained in the object are drawn out and concentrated during heating.

Hereinafter, there is described a method of manufacturing red ginseng extract with decoctor 100 in more specific construction. The method is performed with decoctor 100 comprising: main body 110, heating vessel 120 for storing water, inner vessel 122 having support plate 122a and ginseng, steam collector 130 for gathering steam, water for boiling tank 140 in steam collector 130 for storing water, open/close valve 150 for sending water-for-boiling stored in tank 140 into steam collector 130, solenoid 160 for opening/closing open/close valve 150, means for condensing the steam collected in steam collector 130, and steam/condensed water guiding means for guiding the steam of heating vessel 120 to steam collector 130 and the condensed water of steam collector 130 to heating vessel 120.

The method comprises the steps of: storing water so high as not to cause ginseng (undried or white) to be immersed therein while inner vessel 122 having ginseng is safely positioned in heating vessel 120; storing water in water for boiling tank 140 so high as to cause ginseng contained in heating vessel 120 to be immersed therein; steam-boiling ginseng for a predetermined time by means of steam produced in heating vessel 120 heated; drying steam-boiled ginseng for a predetermined time with heater 114 turned off; opening open/close valve 150 to cause water stored in tank 140 to go into heating vessel 120 so that the steam-boiled and dried ginseng is immersed into the water; and heating heating vessel 120 and re-boiling the steam-boiled and dried ginseng which is immersed into water.

More specifically, in the step of storing a predetermined amount of water in heating vessel 120, ginseng is designed not to be immersed into the water when inner vessel 122 having ginseng is safely placed in heating vessel 120. This is because not steamy but just boiling is performed if ginseng is sunk and heated in water. Here, the amount of water stored in heating vessel 120 is approximately 100 cc.

In the step of storing water for boiling in tank 140, water for boiling is reserved in tank 140 to put it into heating vessel 120 for boiling after steamy boiling. Here, the amount of water in tank is approximately 1,500 cc which is as high as to cause the steam-boiled ginseng to be sufficiently immersed into the water.

In the steamy boiling, ginseng is boiled with steam produced in heating vessel 120 heated while the ginseng is not immersed into water. This is designed to convert (undried or white) ginseng into red. Here, undried ginseng is steam-boiled for about two hours, and white for about five hours.

Through the steamy boiling process several kinds of phenolic compounds and maltol are produced as aging resistants (anti-oxidants), which are contained in red ginseng.

The drying process intends to maintain the useful components generated in ginseng through steamy boiling. This step is carried out for about 30 minutes with heater 114 off.

The step of causing the water for boiling stored in water for boiling tank 140 to go into heating vessel 120 is prepared to proceed the re-boiling of the ginseng steam-boiled and dried. When open/close valve 150 is opened according to solenoid 160, water for boiling stored in tank 140 enters steam collector 130 and then heating vessel 120 through the steam/condensed water guiding means, to thereby immerse the steam-boiled and dried ginseng. In this state re-boiling is performed.

In the re-boiling process, the useful components contained in ginseng steam-boiled and dried by means of heating vessel 120 are extracted and ginsenosides Rg and Rh are produced. Through this step ginseng is boiled and thus becomes red ginseng extract. The time is over 18 hours of ceaseless boiling for the purpose of optimal condition of red ginseng.

From now on, there will be presented the procedure of red ginseng extract according to the method of manufacturing red ginseng extract with the decoctor 100 endowed with steamy boiling function of the invention. First of all, water of 100 cc is poured into heating vessel 120, and inner vessel 122 having ginseng is safely positioned therein. Water for boiling of 1,500 cc is stored in water for boiling tank 140, and then heating vessel 120 is safely placed on heater 114 and heated.

The steam produced in heating vessel 120 steam-boils the ginseng put on support plate 122a of inner vessel 122. During the steamy boiling of ginseng, water in heating vessel 120 circulates heating vessel 120 and steam collector 130 in the form of steam or condensed water through the steam/condensed water guiding means. Here, the water for boiling stored in tank 140 is heated by the steam gathered into steam collector 130 so that the water's temperature rises. This allows the tank 140 to act to cool the steam gathered in steam collector 130.

After steam-boiling of about two hours for undried ginseng and five for white, heater 114 is turned off and drying of about 30 minutes is executed.

After the drying of the ginseng steam-boiled, open/close valve 150 is opened according to solenoid 160 to thereby send the water for boiling stored in tank 140 into steam collector 130. Here, the water for boiling entering steam collector 130 goes into heating vessel 120 through steam/condensed water guiding means so that the steam-boiled and dried ginseng is immersed into the water.

When heating vessel 120 is heated by means of heater 114 while the steam-boiled and dried ginseng is immersed in the water stored in heating vessel 120, the ginseng is re-boiled in water. The re-boiling is executed for over 18 hours for the optimal condition of red ginseng extract.

During the re-boiling the water in heating vessel 120 repeatedly circulates heating vessel 120 and steam collector 130 through the steam/condensed water guiding means in the form of steam or condensed water. In this procedure such healthful components as ginsenosides Rg and Rh are produced and extracted from the ginseng. This is the red ginseng extract.

The red ginseng extract contains useful components produced during the manufacturing of red ginseng from undried. This can obtain red ginseng extract containing its peculiar useful components through steam-boiling, drying and re-boiling of undried or white ginseng without the process of boiling and extracting of red ginseng.

Turning to FIGS. 14, 15 and 16, the embodiment 400 of the decoctor of the invention comprises: a main body 410 of a predetermined size having a heater 414 at an appropriate place; a heating vessel 420 put above heater 414 for heating a to-be-boiled object contained therein; an inner vessel 422 safely placed in heating vessel 420 for supporting the object with its support plate 422a; a water reservoir 430 installed at an appropriate place of main body 410 for storing water to be supplied to heating vessel 420; means for supplying water stored in water reservoir 430 to heating vessel 420; a steam collector 450 for gathering steam produced from heating vessel 420 while the object contained in heating vessel 420 is boiled; means for condensing the steam collected in steam collector 450; and steam/condensed water guiding means for enabling heating vessel 420 to communicate with steam collector 450 when heating vessel 420 is safely placed in main body 410, and thus leading the steam contained in heating vessel 420 to steam collector 450 and the condensed water condensed in steam collector 450 to heating vessel 420.

In the above construction, when heating vessel 420 is heated while water of water reservoir 430 is supplied to heating vessel by means of the water supply means so high that the object contained in heating vessel 420 is not immersed, the object is steamy boiled by means of the steam produced. After the steamy boiling of the object for a predetermined time, the water of reservoir 430 is supplied to heating vessel 420 through the water supply means so high that the object is fully immersed, and then the object is reboiled.

The steam produced from the reboiling process is condensed in the form of liquid, and enters steam collector 450 and then heating vessel 420 through steam/condensed water guiding means. Here, the method of condensing the steam produced is air-cooling.

A method of preparing red ginseng extract using the decoctor 400 comprises the steps of: safely placing support plate 422a in heating vessel 120, the support plate having a plurality of throughholes 422b on which ginseng is put; storing water in heating vessel 420 through the water supply means so high that the ginseng is not immersed; heating heating vessel 420 for the purpose of steamy boiling of ginseng carried out by means of the steam produced for a predetermined time; supplying water to the heating vessel by means of the water supply means so high that the steam-boiled ginseng is immersed; and heating heating vessel 420 while the steam-boiled ginseng contained in heating vessel 420 is immersed in the water entered, for the purpose of reboiling the ginseng for a predetermined time.

In more detail, support plate 422a is safely placed in heating vessel 420, and then ginseng is put on the plate.

While ginseng is put on support plate 422a, water stored in reservoir 430 is sent into heating vessel 420 through the water supply means. Here, the amount of water should be supplied as high as not to immerse the ginseng.

With such processes of steam boiling and re-boiling, ginseng bears several kinds of phenolic compounds and maltol, which are contained in red ginseng as the aging-resistants (anti-oxidants), and ginsenosides Rg and Rh. During the steam boiling of ginseng, there are generated such components as several kinds of phenolic compounds and maltol included in red ginseng as the aging resistants (anti-oxidants). During the re-boiling process ginsenosides Rg and Rh are produced.

Therefore, several kinds of phenolic compounds and maltol, the aging resistants (anti-oxidants), and ginsenosides Rg and Rh, all of which are produced during the steam boiling, drying and reboiling, are drawn out to become red ginseng extract.

For more detailed description of the construction of the air-cooled decoctor of the invention, the connection and operation of components will be recited below. First of all, main body 410 constitutes the exterior of home-style decoctor 400 endowed with steamy boiling function of the invention. The decoctor's components are installed inside or at appropriate places of main body 110. Especially, heater 414 for heating the heating vessel 420 is installed under a heating vessel receiver 412 provided on the front of main body 410 for accepting heating vessel 420.

Heating vessel 420 acts to heat a predetermined amount of stored water by means of heater 414. By doing so, steam is generated in the heating vessel 420.

The inner vessel 422 enables a to-be-boiled object to be positioned therein. On the bottom of inner vessel 422, support plate 422a equipped with a plurality of throughholes 422b is positioned so that the object is placed above the surface of water stored in heating vessel 420. Thus constructed inner vessel 422 is safely placed in heating vessel 420 while the object is positioned on support plate 422a.

The reason why the to-be-boiled object is designed to be positioned above the surface of water stored in heating vessel 420 is to perform steamy boiling which is aimed by the invention. The invention's purpose is accomplished by positioning the to-be-boiled object above water stored by means of support plate 422a of inner vessel 422.

Water reservoir 430 is designed to store water for steam-boiling and re-boiling ginseng, placed at an appropriate place of main body 410.

The water supply means acts to supply water stored in water reservoir 430 to heating vessel 420. This means comprises: a water supply tube 440 connected from water reservoir 430 to steam collector 450; a water supply pump 442 installed at an appropriate place of main body 410 for supplying water stored in water reservoir 430 to steam collector 450 through water supply tube 440; and a controller (not shown) for controlling water supply pump 442 and thus the amount of water entering heating vessel 420.

The steam collector 450 is designed to gather steam produced when heating vessel 420 is heated. The vessel is installed in the upper part of main body 410, and communicates with heating vessel 420 by means of the steam/condensed water guiding means. The steam collected in steam collector 450 is cooled and condensed by means of the steam condensing means.

The steam condensing means condenses the steam gathered in steam collector 450. This means comprises: a condensing tube 460 connected downwards on the side of steam collector 450 for sucking the steam collected in steam collector 450, condensing it in the form of liquid and then causing it to go into steam collector 450; a cooling fan 462 installed at an appropriate place of the main body near condensing tube 460 for cooling condensing tube 460; and a steam discharge tube 464 connected to the bottom end of condensing tube 460 for externally discharging the rest uncondensed steam. Here, condensing tube 460 is made in the form of spring so that incoming steam passes through a predetermined length of path. There is provided at an appropriate place of condensing tube 460 a heat-resistant pin 466 for radiating the heat of condensing tube 460 whose temperature is raised.

The steam/condensed water guiding means 470 leads the steam contained in heating vessel 420 and produced when it is heated, into steam collector 450, and the condensed water made in steam collector 450 into heating vessel 420. This means comprises: upper and lower support members 472 and 474 vertically and respectively having steam guiding holes 472*a* and 474*a* at their centers and screw-fastened with the bottom of steam collector 450 being interposed; a steam guiding portion 476 which communicates with steam hole 424*a* formed in heating vessel lid 424, the portion for leading the steam contained in heating vessel 420 to steam collector 450 and the condensed water stored in steam collector 450 to heating vessel 420; a support shaft 476*a* vertically formed at an appropriate position inside steam guiding portion 476 and vertically and movably inserted into steam guiding holes 472*a* and 474*a* of upper and lower support members 472 and 474; an open/close member 478 fastened at the top of support shaft 476*a* for opening or closing the top of the steam guiding hole 472*a* of upper support member 472 and allowing steam guiding portion 476 and support shaft 476*a* to be supported by upper and lower support members 472 and 474 when steam guiding portion 476 moves up and down; and a resilient spring 480 for executing its force to enable steam guiding portion 184 usually to return to the original position.

In more detail, upper support member 472 is formed vertically with steam guiding hole 472*a* at its center. In the lower part of support member 472 a male screw is formed so that the support member passes from the inner center to the outer bottom of the steam collector 450.

Lower support member 474 has steam guiding hole 474*a* vertically penetrated in relation to steam guiding hole 472*a* of upper support member 472. A female screw is formed on the inner circumference of steam guiding hole 474*a* in relation to the male screw of upper support member 472. With the male and female screws, the lower support member is fastened with upper support member 472 at the bottom of steam collector 450. Steam guiding holes 472*a* and 474*a* of respective members 472 and 474 communicate vertically due to the vertical fastening between upper and lower support members 472 and 474 interposed with the bottom of steam collector 450. In other words, the lower center of steam collector 450 stays open through respective steam guiding holes 472*a* and 474*a* of upper and lower support members 472 and 474.

Steam guiding portion 476 leads the steam of heating vessel 420 to steam collector 450 through steam guiding hole 474*a* of lower support member 474 and the condensed water of steam collector 450 to heating vessel 420. The steam guiding portion leads the steam or condensed water through steam guiding hole 476*b* making a sheet-contact with steam hole 424*a* formed in the heating vessel lid 424 and thus vertically penetrated therewith. The steam guiding portion 476 is positioned under lower support member 474 while propped up by support shaft 476*a* vertically formed on the inner top of the portion and by open/close member 478 fastened to the top of support shaft 476*a*.

Formed vertically on the inner top surface of steam guiding portion 476, support shaft 476*a* is penetratingly inserted into respective steam guiding holes 472*a* and 474*a* of upper and lower support members 472 and 474 so that steam guiding portion 476 is designed to move vertically only along the center line of steam guiding holes 472*a* and 474*a* for a predetermined distance. Depending upon the presence or absence of heating vessel 420, steam guiding portion 476 moves vertically along respective steam guiding holes 472*a* and 474*a* of upper and lower support members 472 and 474, and is thus guided vertically only along the center line of steam guiding holes 472*a* and 474*a*.

Open/close member 478 is fastened to the top of support shaft 476*a* penetrating through respective steam guiding holes 472*a* and 474*a* of upper and lower support members 472 and 474 and protruded from the top of steam guiding hole 472*a* of upper support member 472. Made of resilient deformable synthetic resin, the open/close member enables steam guiding portion 476 and support shaft 476*a* to be supported by upper and lower support members 472 and 474. Especially, rubber is favorable for the member 478.

In addition to the function of allowing steam guiding portion 476 and support shaft 476*a* to be supported by upper and lower support members 472 and 474, open/close member 478 has a function of opening or closing the top of steam guiding hole 472*a* of upper support member 472 according to the presence or absence of heating vessel 420. Specifically, open/close member 478 opens or closes steam guiding hole 472*a* placed on the top of upper support member 472 according to the vertical movement of steam guiding portion 476, the movement depending upon the presence or absence of heating vessel 420.

The opening of the top of steam guiding hole 472*a* of upper support member 472 means that the steam of heating vessel 420 goes into steam collector 450 and the condensed water of steam collector 450 into heating vessel 420. When the top of steam guiding hole 472*a* of upper support member 472 is closed, steam or condensed water cannot be guided therethrough.

When support shaft 476*a* penetrates respective steam guiding holes 472*a* and 474*a* of upper and lower support members 472 and 474 and open/close member 478 is fastened to the top of support shaft 476 protruded from the top of steam guiding hole 472 of upper support member 472, support shaft 476a placed between open/close member 478 and steam guiding portion 476 is longer than respective steam guiding holes 472a and 474a of upper and lower support members 472 and 474 so that support shaft 476a moves vertically by the difference. In other words, steam guiding portion 476 can move by the difference between the length of support shaft 476a placed between open/close member 478 and steam guiding portion 476, and the length of upper and lower support member 472 and 474 and steam guiding holes 472a and 474a.

Elastic spring 480 executes its force in the direction of returning steam guiding portion 476 to its original position. Therefore, when the force of raising steam guiding portion 476 disappears, it is made to instantly return to the original position. Installed between lower support member 474 and steam guiding portion 476, spring 480 always executes its force to return steam guiding portion 476 to the original position and thus allow the top surface of heating vessel lid 424 to come into close contact with the bottom surface of steam guiding portion 476.

As shown in FIGS. 17 and 18, the decoctor 400 further comprises means for arresting the vertical movement of steam guiding portion 476. This means consists of: an annular arrestor 490 provided on the outer circumference of steam guiding portion 476 and having a slant guiding surface 490a; a rotary member 492 having another slant surface 492a relative with slant guiding surface 490a; a lever 494 connected to one side of rotary member 492 and externally protruded from the main body; and a rotary member support member 496.

More specifically, annular arrestor 490 is formed on the outer circumference of steam guiding portion 476, and there is formed spirally cut slant guiding surface 490a on the bottom end of the arrestor. Rotary member 492 is formed to be fastened with steam guiding portion 476 while in contact with the bottom surface of annular arrestor 490. The top surface of rotary member 492 has slant surface 492a in relation with slant guiding surface 490a of annular arrestor 490. Provided on the outer circumference of rotary member 492, one end of lever 494 is externally protruded from main body 410 to swivel left and right within a predetermined range. Rotary member support member 496 causes rotary member 492 to turn only at its position so that steam guiding portion 476 moves vertically.

The operation of the steam guiding portion arresting means is explained below when heating vessel 420 is not put on heater 414. Lever 494 is rotated in one direction as in FIG. 18a, and steam guiding portion 476 is moved upward according to the action of slant guiding surface 490a of annular arrestor 490 and slant surface 492a of rotary member 492. Here, plural elastic springs 480 stay compressed.

In this state, when heating vessel 420 is mounted on heater 414 and lever 494 is rotated in the other direction, rotary member 492 is turned reversely and steam guiding portion 476 moves downwards due to the resilient force of elastic springs 480 so that it comes into sheet-contact with steam hole 424a formed on heating vessel lid 424. This state allows the steam of heating vessel 420 to enter steam collector 450 and the condensed water of steam collector 450 to enter heating vessel 420.

The decoctor 400 further comprises a falling water receiver 500 placed at an appropriate position of heater 414 so that the boiling solution falling from steam/condensed water guiding means 470 can be collected when heating vessel 420 is detached from main body 410.

The operation of air-cooled decoctor 400 is described from now on. After a predetermined amount of water (approximately 2,000 cc) is stored in water reservoir 430 and when decoctor 400 is turned on, water supply pump 442 is operated so that the water stored in water reservoir 430 goes into steam collector 450 through water supply tube 440 and then the water entering steam collector 450 into heating vessel 420 through steam/condensed guiding means 470. Here, the water supplied is as much (approximately 500 cc) as not to cause ginseng to be immersed thereinto.

In this condition, when heating vessel 420 is heated for a predetermined time by means of heater 414, steam is produced while ginseng is steam-boiled. This steam goes into steam collector 450 through steam/condensed water guiding means 470. The steam entering steam collector 450 then goes into condensing tube 460 and is condensed in the form of liquid. This condensed liquid goes back into steam collector 450 and into heating vessel 420 through steam/condensed water guiding means 470. Here, cooling fan 462 continuously cools condensing tube 460 and heat-resistant pin 466 so as to maintain the condensing effect of steam.

After the steam-boiling of ginseng by means of heating for a predetermined time, water supply pump 442 is driven according to the controller so that remaining water (about 1,500 cc) stored in water reservoir 430 is sent to heating vessel 420 through water supply tube 440, steam collector 450 and steam/condensed water guiding means 470. Here, the water supplied to heating vessel 420 causes the steam-boiled ginseng to be immersed completely.

With such processes of steam boiling and re-boiling, ginseng bears several kinds of phenolic compounds and maltol, which are contained in red ginseng as the aging-resistants (anti-oxidants), and ginsenosides Rg and Rh. During the steam boiling of ginseng, there are generated such components as several kinds of phenolic compounds and maltol included in red ginseng as the aging resistants (anti-oxidants). During the re-boiling process ginsenosides Rg and Rh are produced.

As above, through steam-boiling, drying and re-boiling of undried or white ginseng with home-style decoctor 100 endowed with steamy boiling function of the present invention, the undried or white ginseng becomes red ginseng extract, which possesses several kinds of phenolic compounds, and maltol, anti-oxidants, and ginsenosides Rg and Rh. This allows red ginseng extract to be made domestically with ease.

In addition, the embodiments of decoctor of the invention can also manufacture red ginseng extract by drawing out useful components from red ginseng through its steam-boiling, drying and re-boiling. Especially, for red ginseng, red ginseng extract containing useful components can be obtained only through reboiling without steam-boiling or drying process.

As described above, the home-style decoctor endowed with steamy boiling function of the present invention offers two functions of steam-boiling and simple boiling, facilitating its use.

For another effect of the present invention, undried or white ginseng can become red ginseng extract by producing such useful components as several kinds of phenolic compounds and maltol, anti-oxidants, and ginsenosides Rg and Rh through steam-boiling, drying and re-boiling.

For still another effect of the present invention, with the steam guiding portion and heating vessel lid tightened by means of a sealing member, the leakage of steam as well as the loss of boiling solution can be prevented during boiling.

No steam leakage can prevent the decoctor surface from being contaminated with oozing steam.

It will be apparent to the reader that the foregoing description of the invention has been presented for purposes of illustration and description and for providing an understanding of the invention and that many changes and modifications can be made without departing from the scope of the invention. It is therefore intended that the scope of the invention be indicated by the appended claims rather than by the foregoing description; and all changes which come within the meaning and range of equivalency of the claims are therefore intended to be embraced therein.

What is claimed is:

1. A home-style decoctor endowed with steamy boiling function, the decoctor being comprised of:
    a main body of a predetermined size equipped with a heater at an appropriate position of the bottom;
    a heating vessel for containing and heating a predetermined amount of water with the heater;
    a support plate having a plurality of throughholes and for allowing a to-be-boiled object to be placed above the surface of water stored in the heating vessel and to be steam-boiled with the steam produced inside the heating vessel;
    means for supplying water for boiling into the heating vessel so that the to-be-boiled-object is immersed after its steamy boiling and drying;
    a steam collector for gathering steam produced when the to-be-boiled object is decocted with the water for boiling;
    means for condensing the steam collected into the steam collector; and
    steam/condensed water guiding means for causing the heating vessel to communicate with the steam collector when the heating vessel is safely placed in the main body and thus leading the steam present in the heating vessel to the steam collector and the condensed water placed in the steam collector to the heating vessel.

2. A home-style decoctor endowed with a steamy boiling function as claimed in claim 1, further comprising: an open/close valve installed in the upper portion of the steam collector, the valve being opened when the steam collector's internal pressure is raised above a predetermined point so that the steam contained in the steam collector is discharged externally.

3. A home-style decoctor as claimed in claim 1, wherein the water-for-boiling supplying means comprises:
    a water for boiling tank installed to be spaced apart upward from the inner bottom of the steam collector for storing so much an amount as to cause the to-be-boiled object contained in the heating vessel to be immersed;
    an open/close valve installed at an appropriate position of the bottom of the tank for discharging the water for boiling into the steam collector according to the opening/closing action;
    means installed at an appropriate position of the main body placed under the open/close valve for opening or closing the open/close valve.

4. A home-style decoctor as claimed in claim 3, wherein the open/close valve opening/closing means is a solenoid.

5. A home-style decoctor as claimed in claim 1, wherein the steam condensing means comprises:
    a cooling water reservoir installed at an appropriate position of the main body for storing cooling water;
    a cooling water circulation tube installed spirally on the circumference of the steam collector for allowing the cooling water stored in the cooling water reservoir to flow;
    a cooling water circulation pump for forcibly circulating the cooling water stored in the cooling water reservoir into the cooling water circulation tube; and
    a heat-resistant pin installed at an appropriate place of the cooling water circulation tube for radiating heat of the cooling water whose temperature is raised.

6. A home-style decoctor endowed with steamy boiling function as claimed in claim 5, the decoctor further comprising: a cooling water residual indicator provided at an appropriate place of one side of the main body for confirming the residual of cooling water contained in the cooling water reservoir.

7. A home-style decoctor endowed with steamy boiling function as claimed in claim 5, the decoctor further comprising: a cooling fan installed at an appropriate place of the main body near the heat-resistant pin for cooling it.

8. A home-style decoctor endowed with steamy boiling function as claimed in claim 7, the decoctor further comprising: means for detecting the temperatures of the steam collector and the cooling water circulation tube if the cooling water circulation pump or the cooling fan has a problem, the means deciding that there occurs trouble therein if the temperatures reach a predetermined point, and thus turning off the heater to thereby prevent its overheating.

9. A home-style decoctor endowed with steamy boiling function as claimed in claim 8, wherein the overheating preventive means comprises:
    a temperature detecting portion installed on one side of the steam collector for detecting its temperature;
    a comparing portion for comparing the temperature of the steam collector detected by the temperature detecting portion with a predetermined point;
    a controller for, if the temperature of the steam collector goes above a predetermined point, deciding that the cooling water circulation pump or the cooling fan has a problem to thereby turn off the power of the heater, the controller further controlling the general operations of the decoctor; and
    an alarm for generating an alarm which can be recognized by an user when it is decided by the controller that the cooling water circulation pump or the cooling fan has trouble.

10. A home-style decoctor endowed with steamy boiling function as claimed in claim 9, wherein the alarm is a buzzer which can be aurally recognized by its user.

11. A home-style decoctor endowed with steamy boiling function as claimed in claim 9, wherein the alarm is an on-and-off light which can be visually recognized by its user.

12. A home-style decoctor endowed with steamy boiling function as claimed in claim 1, wherein the steam/condensed water guiding means comprises:
    upper and lower support members vertically and respectively having penetrating steam guiding holes at their centers and screw-fastened with the bottom of the steam collector being interposed;
    a steam guiding portion which communicates with the steam hole formed in the heating vessel lid, the portion for leading the steam contained in the heating vessel to the steam collector and the condensed water stored in the steam collector to the heating vessel;
    a support shaft vertically formed at an appropriate position inside the steam guiding portion and vertically and movably inserted into the steam guiding holes of the upper and lower support members;
    an open/close member fastened at the top of the support shaft for opening or closing the top of the steam guiding hole of the upper support member and allowing the steam guiding portion and the support shaft to be supported by the upper and lower support members when the steam guiding portion moves up and down;

an elastic wavy tube installed on the circumference of the support shaft and whose top and bottom surfaces come into tight contact with the bottom of the lower support member and the inner top of the steam guiding portion, respectively, the tube for leading the steam contained in the heating vessel to the steam collector and the condensed water stored in the steam collector to the heating vessel through the steam guiding portion; and a resilient spring installed at the circumference of the wavy tube for allowing the top and bottom of the wavy tube to come into close contact with the bottom of the lower support member and the inner top of the steam guiding portion, the spring executing its force to enable the steam guiding portion usually to return to the original position.

13. A home-style decoctor endowed with steamy boiling function as claimed in claim 12, the decoctor further comprising a sealing member provided on the bottom of the steam guiding portion, the member preventing the leakage of steam by tightening the border of the steam hole of the heating vessel lid and the bottom of the steam guiding portion.

14. A home-style decoctor endowed with steamy boiling function as claimed in claim 12, the decoctor further comprising means for arresting the vertical movement of the steam guiding portion.

15. A home-style decoctor endowed with steamy boiling function as claimed in claim 14, wherein the steam guiding portion movement arresting means comprises:

a stop formed on the circumference of the steam guiding portion;

a pushing member one end of which is protruded outward from the main body, the member rectilinearly and horizontally moving;

a spring whose force is executed to enable the pushing member always to be protruded outward; and an arresting member installed to be rotable inward and outward horizontally at an appropriate position and on both sides in the main body, one end of the member being hinged on the other end of the pushing member, the member moving inward and outward while engaging with the pushing member which moves horizontally, to be thereby caught or released from the stop of the steam guiding portion.

16. A home-style decoctor endowed with steamy boiling function as claimed in claim 1, the decoctor further comprising falling water receiver means placed at an appropriate position of the heater for withdrawing boiling solution falling from the steam/condensed guiding means when the heating vessel is detached from the main body.

17. A home-style decoctor endowed with steamy boiling function as claimed in claim 16, wherein the falling water receiver means comprises:

an outer cask installed at an appropriate place inside the heater on the central line of the steam/condensed guiding means;

a falling water receiver detachably installed on the inner side of the outer cask for collecting boiling solution falling from the steam/condensed water guiding means; and a handle formed on the inner central bottom of the falling water receiver and used to allow the barrel to separate from the outer cask.

18. A home-style decoctor endowed with steamy boiling function as claimed in claim 17, wherein the bottom of the barrel is formed conically to minimize the heat transmission from the outer cask.

19. A home-style decoctor endowed with steamy boiling function as claimed in claim 17, wherein the decoctor further comprising:

a plurality of contact preventive bumps protuberantly formed on the inner side of the outer cask for causing the outer circumference of the barrel to come into no sheet-contact with the inner circumference of the outer cask when the barrel is safely positioned in the outer cask.

20. A home-style decoctor endowed with steamy boiling function as claimed in claim 13, the decoctor further comprising means for arresting the vertical movement of the steam guiding portion.

21. A home-style decoctor endowed with steamy boiling function as claimed in claim 18, the decoctor further comprising:

a plurality of contact preventive bumps protuberantly formed on the inner side of the outer cask for causing the outer circumference of the barrel to come into no sheet-contact with the inner circumference of the outer cask when the barrel is safely positioned in the outer cask.

22. A home-style decoctor endowed with steamy boiling function comprising:

a main body of a predetermined size having a heater at an appropriate place of its bottom;

a heating vessel put above the heater for heating a to-be-boiled object contained therein;

a support plate having a plurality of throughholes mounted on the heater for supporting a to-be-boiled object so that it is located above water stored, the plate allowing the object to be steam-boiled by means of steam produced inside the heating vessel; a water reservoir installed at an appropriate place of the main body for storing water to be supplied to the heating vessel;

means for supplying water stored in the water reservoir to the heating vessel;

a steam collector for gathering steam produced from the heating vessel while the object contained in the heating vessel is boiled;

means for condensing the steam collected in the steam collector; and steam/condensed water guiding means for enabling the heating vessel to communicate with the steam collector when the heating vessel is safely placed in the main body, and thus leading the steam contained in the heating vessel to the steam collector and the water condensed in the steam collector to the heating vessel.

23. A home-style decoctor endowed with a steam-boiling function as claimed in claim 22, wherein the water supply means comprises:

a water supply tube connected from the water reservoir to the steam collector;

a water supply pump installed at an appropriate place of the main body for supplying water stored in the water reservoir to the steam collector through the water supply tube; and a controller for controlling the water supply pump and thus the amount of water entering the heating vessel.

24. A home-style decoctor endowed with a steam boiling function as claimed in claim 22, wherein the steam condensing means comprises:

a condensing tube connected downwards on the side of the steam collector for sucking the steam collected in the steam collector, condensing it in the form of liquid and then causing it to go into the steam collector;

a cooling fan installed at an appropriate place of the main body near the condensing tube for cooling the condensing tube; and a steam discharge tube connected to the bottom end of the condensing tube for externally discharging the rest uncondensed steam.

25. A home-style decoctor endowed with a steam boiling function as claimed in claim 24, wherein the condensing tube is made in the form of spring so that incoming steam passes through a path of a predetermined length.

26. A home-style decoctor endowed with a steam boiling function as claimed in claim 24, further comprising a heat-resistant pin installed at an appropriate place of the condensing tube for irradiating heat of the condensing tube whose temperature is raised.

27. A home-style decoctor endowed with a steam boiling function as claimed in claim 22, wherein the steam/condensed water guiding means comprises:

upper and lower support members vertically and respectively having steam guiding holes at their centers and screw-fastened with the bottom of the steam collector being interposed;

a steam guiding portion which communicates with the steam hole formed in the heating vessel lid, the portion for leading the steam contained in the heating vessel to the steam collector and the condensed water stored in the steam collector to the heating vessel 420;

a support shaft vertically formed at an appropriate position inside the steam guiding portion and vertically and movably inserted into the steam guiding holes of the upper and lower support members;

an open/close member fastened at the top of the support shaft for opening or closing the top of the steam guiding hole of the upper support member and allowing the steam guiding portion and the support shaft to be supported by the upper and lower support members when the steam guiding portion moves up and down; and a resilient spring for executing its force to enable the steam guiding portion usually to return to the original position.

28. A home-style decoctor endowed with a steam boiling function as claimed in claim 27, the decoctor further comprising means for arresting the vertical movement of the steam guiding portion.

29. A home-style decoctor endowed with a steam boiling function as claimed in claim 28, wherein the steam guiding portion movement arresting means comprises:

an annular arrestor provided on the outer circumference of the steam guiding portion and having a slant guiding surface;

a rotary member having another slant surface relative with a slant guiding surface;

a lever connected to one side of the rotary member and externally protruded from the main body; and a rotary member support member, whereby the lever moves left and right to allow the rotary member to turn left and right and thus the steam guiding portion to move up and down.

30. A home-style decoctor endowed with a steam boiling function as claimed in claim 22, the decoctor further comprising falling water receiver means provided at an appropriate place of the heater so that re-boiling solution falling from the steam/condensed guiding means is withdrawn when the heating vessel is detached from the main body.

31. A home-style decoctor endowed with a steam boiling function as claimed in claim 25, further comprising a heat-resistant pin installed at an appropriate place of the condensing tube for irradiating heat of the condensing tube whose temperature is raised.

* * * * *